United States Patent
Weber et al.

(10) Patent No.: US 10,357,206 B2
(45) Date of Patent: Jul. 23, 2019

(54) VARIABLE INDICATION ESTIMATOR

(71) Applicant: MASIMO CORPORATION, Irvine, CA (US)

(72) Inventors: Walter M. Weber, Laguna Hills, CA (US); Ammar Al-Ali, Tustin, CA (US); Lorenzo Cazzoli, Barcelona (ES)

(73) Assignee: MASIMO CORPORATION, Irvine, CA (US)

(*) Notice: Subject to any disclaimer, the term of this patent is extended or adjusted under 35 U.S.C. 154(b) by 0 days.

(21) Appl. No.: 15/913,044

(22) Filed: Mar. 6, 2018

(65) Prior Publication Data

US 2018/0256113 A1 Sep. 13, 2018

Related U.S. Application Data

(63) Continuation of application No. 14/830,211, filed on Aug. 19, 2015, now abandoned, which is a
(Continued)

(51) Int. Cl.
*A61B 5/00* (2006.01)
*A61B 5/021* (2006.01)
(Continued)

(52) U.S. Cl.
CPC .......... *A61B 5/7271* (2013.01); *A61B 5/0002* (2013.01); *A61B 5/021* (2013.01);
(Continued)

(58) Field of Classification Search
CPC ..... A61B 5/7271; A61B 5/6829; A61B 5/021; A61B 5/14551; A61B 5/6838;
(Continued)

(56) References Cited

U.S. PATENT DOCUMENTS

| 4,051,522 A | 9/1977 | Healy |
|---|---|---|
| 4,085,378 A | 4/1978 | Ryan |

(Continued)

FOREIGN PATENT DOCUMENTS

| DE | 3328862 | 2/1985 |
|---|---|---|
| EP | 0104771 | 4/1984 |

(Continued)

OTHER PUBLICATIONS

Blitt, Casey D., Monitoring in Anesthesia and Critical Care Medicine, (2d ed. 1990).

(Continued)

*Primary Examiner* — Yoshihisa Ishizuka
(74) *Attorney, Agent, or Firm* — Knobbe, Martens, Olson & Bear, LLP

(57) ABSTRACT

A variable indication estimator which determines an output value representative of a set of input data. For example, the estimator can reduce input data to estimates of a desired signal, select a time, and determine an output value from the estimates and the time. In one embodiment, the time is selected using one or more adjustable signal confidence parameters determine where along the estimates the output value will be computed. By varying the parameters, the characteristics of the output value are variable. For example, when input signal confidence is low, the parameters are adjusted so that the output value is a smoothed representation of the input signal. When input signal confidence is high, the parameters are adjusted so that the output value has a faster and more accurate response to the input signal.

16 Claims, 13 Drawing Sheets

Related U.S. Application Data continuation of application No. 13/942,562, filed on Jul. 15, 2013, now Pat. No. 9,138,192, which is a continuation of application No. 13/601,930, filed on Aug. 31, 2012, now Pat. No. 8,489,364, which is a continuation of application No. 13/007,109, filed on Jan. 14, 2011, now Pat. No. 8,260,577, which is a continuation of application No. 12/362,463, filed on Jan. 29, 2009, now Pat. No. 7,873,497, which is a continuation of application No. 11/375,662, filed on Mar. 14, 2006, now Pat. No. 7,499,835, which is a continuation of application No. 10/213,270, filed on Aug. 5, 2002, now Pat. No. 6,999,904, which is a continuation-in-part of application No. 09/586,845, filed on Jun. 5, 2000, now Pat. No. 6,430,525.

(51) Int. Cl.
  *A61B 5/1455* (2006.01)
  *G06K 9/00* (2006.01)

(52) U.S. Cl.
  CPC ........ *A61B 5/14551* (2013.01); *A61B 5/6826* (2013.01); *A61B 5/6829* (2013.01); *A61B 5/6838* (2013.01); *A61B 5/72* (2013.01); *G06K 9/0051* (2013.01); *A61B 5/1455* (2013.01); *A61B 5/7207* (2013.01); *A61B 5/7239* (2013.01)

(58) Field of Classification Search
  CPC ....... A61B 5/0002; A61B 5/6826; A61B 5/72; A61B 5/7239; A61B 5/1455; A61B 5/7207; G06K 9/0051
  USPC ........................................................ 702/185
  See application file for complete search history.

(56) References Cited

U.S. PATENT DOCUMENTS

| | | |
|---|---|---|
| 4,623,248 A | 11/1986 | Sperinde |
| 4,653,498 A | 3/1987 | New et al. |
| 4,745,398 A | 5/1988 | Abel |
| 4,765,340 A | 8/1988 | Sakai |
| 4,800,495 A | 1/1989 | Smith |
| 4,802,486 A | 2/1989 | Goodman |
| 4,863,265 A | 9/1989 | Flower et al. |
| 4,870,588 A | 11/1989 | Merhav |
| 4,911,167 A | 3/1990 | Corenman et al. |
| 4,934,372 A | 6/1990 | Corenman et al. |
| 4,942,877 A | 7/1990 | Sakai |
| 4,955,379 A | 9/1990 | Hall |
| 4,960,128 A | 10/1990 | Gordon et al. |
| 4,964,408 A | 10/1990 | Hink et al. |
| 4,965,840 A | 10/1990 | Subbarao |
| 5,003,252 A | 3/1991 | Nystrom |
| 5,018,088 A | 5/1991 | Higbie |
| RE33,643 E | 7/1991 | Isaacson et al. |
| 5,041,187 A | 8/1991 | Hink et al. |
| 5,056,052 A | 10/1991 | Wick et al. |
| 5,069,213 A | 12/1991 | Polczynski |
| 5,136,267 A | 8/1992 | Cabot |
| 5,163,438 A | 11/1992 | Gordon et al. |
| 5,170,791 A | 12/1992 | Boos et al. |
| 5,188,108 A | 2/1993 | Secker |
| 5,190,038 A | 3/1993 | Polson |
| 5,193,124 A | 3/1993 | Subbarao |
| 5,218,962 A | 6/1993 | Mannheimer |
| 5,226,417 A | 7/1993 | Swedlow |
| 5,246,002 A | 9/1993 | Prosser |
| 5,259,381 A | 11/1993 | Cheung |
| 5,270,942 A | 12/1993 | Reed |
| 5,278,627 A | 1/1994 | Aoyagi et al. |
| 5,303,702 A | 4/1994 | Bonnet |
| 5,307,284 A | 4/1994 | Brunfeldt |
| 5,331,394 A | 7/1994 | Shalon et al. |
| 5,337,744 A | 8/1994 | Branigan |
| 5,341,805 A | 8/1994 | Stavridi et al. |
| 5,345,510 A | 9/1994 | Singhi |
| 5,353,356 A | 10/1994 | Waugh et al. |
| 5,355,882 A | 10/1994 | Ukawa et al. |
| 5,357,965 A | 10/1994 | Hall et al. |
| 5,368,224 A | 11/1994 | Richardson |
| D353,195 S | 12/1994 | Savage et al. |
| D353,196 S | 12/1994 | Savage et al. |
| 5,377,676 A | 1/1995 | Vari et al. |
| 5,384,451 A | 1/1995 | Smith et al. |
| 5,398,003 A | 3/1995 | Heyl et al. |
| 5,404,003 A | 4/1995 | Smith |
| 5,406,952 A | 4/1995 | Barnes |
| D359,546 S | 6/1995 | Savage et al. |
| 5,421,329 A | 6/1995 | Casciani |
| 5,431,170 A | 7/1995 | Matthews |
| D361,840 S | 8/1995 | Savage et al. |
| 5,438,983 A | 8/1995 | Flacone |
| 5,442,940 A | 8/1995 | Secker et al. |
| D362,063 S | 9/1995 | Savage et al. |
| 5,448,991 A | 9/1995 | Polson |
| 5,452,717 A | 9/1995 | Branigan et al. |
| D363,120 S | 10/1995 | Savage et al. |
| 5,456,252 A | 10/1995 | Vari et al. |
| 5,481,620 A | 1/1996 | Vaidyanathan |
| 5,482,036 A | 1/1996 | Diab et al. |
| 5,490,505 A | 2/1996 | Diab et al. |
| 5,494,043 A | 2/1996 | O'Sullivan et al. |
| 5,503,148 A | 4/1996 | Pologe et al. |
| 5,511,042 A | 4/1996 | O'Brien, Jr. |
| 5,533,511 A | 7/1996 | Kaspari et al. |
| 5,542,421 A | 8/1996 | Erdman |
| 5,549,111 A | 8/1996 | Wright et al. |
| 5,558,096 A | 9/1996 | Palatnik |
| 5,561,275 A | 10/1996 | Savage et al. |
| 5,562,002 A | 10/1996 | Lalin |
| 5,575,284 A | 11/1996 | Athan et al. |
| 5,588,435 A | 12/1996 | Weng et al. |
| 5,590,649 A | 1/1997 | Caro et al. |
| 5,602,924 A | 2/1997 | Durand et al. |
| 5,608,820 A | 3/1997 | Vaidyanathan |
| 5,610,996 A | 3/1997 | Eller |
| 5,626,140 A | 5/1997 | Feldman et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,060 A | 7/1997 | Yorkey |
| 5,645,440 A | 7/1997 | Tobler et al. |
| 5,652,566 A | 7/1997 | Lambert |
| 5,685,299 A | 11/1997 | Diab et al. |
| 5,697,958 A | 12/1997 | Paul |
| 5,720,293 A | 2/1998 | Quinn |
| D393,830 S | 4/1998 | Tobler et al. |
| 5,743,262 A | 4/1998 | Lepper, Jr. et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,237 A | 7/1998 | Casciani |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,820,267 A | 10/1998 | Bryars |
| 5,823,950 A | 10/1998 | Diab et al. |
| 5,830,131 A | 11/1998 | Caro et al. |
| 5,833,618 A | 11/1998 | Caro et al. |
| 5,842,979 A | 12/1998 | Jarman |
| 5,853,364 A | 12/1998 | Baker et al. |
| 5,856,934 A | 1/1999 | Nakajima et al. |
| 5,860,919 A | 1/1999 | Kiani-Azarbayjany et al. |
| 5,865,736 A | 2/1999 | Baker, Jr. et al. |
| 5,890,929 A | 4/1999 | Mills et al. |
| 5,891,023 A | 4/1999 | Lynn |
| 5,904,654 A | 5/1999 | Wholtmann et al. |
| 5,919,134 A | 7/1999 | Diab |

(56) References Cited

U.S. PATENT DOCUMENTS

| | | |
|---|---|---|
| 5,921,921 A | 7/1999 | Potratz et al. |
| 5,934,277 A | 8/1999 | Mortz |
| 5,934,925 A | 8/1999 | Tobler et al. |
| 5,940,182 A | 8/1999 | Lepper, Jr. et al. |
| 5,950,139 A | 9/1999 | Korycan |
| 5,957,866 A | 9/1999 | Shapiro et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,041,290 A | 3/2000 | Matt et al. |
| 6,045,509 A | 4/2000 | Caro et al. |
| 6,047,203 A | 4/2000 | Sackner et al. |
| 6,064,910 A | 5/2000 | Andersson et al. |
| 6,067,462 A | 5/2000 | Diab et al. |
| 6,081,735 A | 6/2000 | Diab et al. |
| 6,083,172 A | 7/2000 | Baker et al. |
| 6,088,607 A | 7/2000 | Diab et al. |
| 6,094,592 A | 7/2000 | Yorkey et al. |
| 6,094,627 A | 7/2000 | Peck et al. |
| 6,108,610 A | 8/2000 | Winn |
| 6,110,522 A | 8/2000 | Lepper, Jr. et al. |
| 6,119,026 A | 9/2000 | McNulty et al. |
| 6,122,535 A | 9/2000 | Kaestle et al. |
| 6,124,597 A | 9/2000 | Shehada |
| 6,135,952 A | 10/2000 | Coetzee |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,188,407 B1 | 2/2001 | Smith et al. |
| 6,206,830 B1 | 3/2001 | Diab et al. |
| 6,216,021 B1 | 4/2001 | Franceschini et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,321,100 B1 | 11/2001 | Parker |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali et al. |
| 6,388,240 B2 | 5/2002 | Schulz et al. |
| 6,397,091 B2 | 5/2002 | Diab et al. |
| 6,408,198 B1 | 6/2002 | Hanna et al. |
| 6,430,525 B1 | 8/2002 | Weber et al. |
| 6,438,401 B1 | 8/2002 | Cheng et al. |
| 6,463,311 B1 | 10/2002 | Diab |
| 6,470,199 B1 | 10/2002 | Kopotic et al. |
| 6,501,975 B2 | 12/2002 | Diab |
| 6,505,059 B1 | 1/2003 | Kollias et al. |
| 6,515,273 B2 | 2/2003 | Al-Ali et al. |
| 6,519,486 B1 | 2/2003 | Edgar et al. |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,575,905 B2 | 6/2003 | Knobbe et al. |
| 6,580,086 B1 | 6/2003 | Schulz et al. |
| 6,584,336 B1 | 6/2003 | Ali et al. |
| 6,594,512 B2 | 7/2003 | Huang |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Diab et al. |
| 6,661,161 B1 | 12/2003 | Lanzo et al. |
| 6,671,531 B2 | 12/2003 | Al-Ali et al. |
| 6,675,031 B1 | 1/2004 | Porges et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,754,516 B2 | 6/2004 | Mannheimer |
| 6,760,607 B2 | 7/2004 | Al-Ali |
| 6,763,256 B2 | 7/2004 | Kimball et al. |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 2/2006 | Dalke et al. |
| 7,024,233 B2 | 4/2006 | Al-Ali et al. |
| 7,027,849 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,213,950 B1 | 5/2007 | Lawrence |
| 7,215,984 B2 | 5/2007 | Diab |
| 7,215,986 B2 | 5/2007 | Diab |
| 7,221,971 B2 | 5/2007 | Diab |

(56) References Cited

U.S. PATENT DOCUMENTS

| | | |
|---|---|---|
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,457,652 B2 | 11/2008 | Porges et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 8,133,176 B2 | 3/2012 | Porges et al. |
| 8,260,577 B2 | 9/2012 | Weber et al. |
| 2002/0082488 A1 | 6/2002 | Al-Ali |
| 2002/0161291 A1 | 10/2002 | Kiani |
| 2003/0000522 A1 | 1/2003 | Lynn |
| 2003/0018241 A1 | 1/2003 | Mannheimer |
| 2003/0073890 A1 | 4/2003 | Hanna |
| 2003/0120164 A1 | 6/2003 | Nielsen |
| 2004/0097797 A1 | 5/2004 | Porges et al. |
| 2006/0030764 A1 | 2/2006 | Porges et al. |

FOREIGN PATENT DOCUMENTS

| | | |
|---|---|---|
| EP | 0352923 | 1/1990 |
| EP | 0645117 | 3/1995 |
| EP | 0659384 | 6/1995 |
| WO | WO 84/03032 | 8/1984 |
| WO | WO 92/11803 | 7/1992 |
| WO | WO 92/15955 | 9/1992 |
| WO | WO 92/20273 | 11/1992 |
| WO | WO 95/02288 | 1/1995 |
| WO | WO 95/21567 | 8/1995 |
| WO | WO 96/12435 | 5/1996 |
| WO | WO 98/43071 | 10/1998 |

OTHER PUBLICATIONS

Boualem Boashash, Estimating and Interpreting the Instantaneous Frequency of a Signal-Part I: Fundamentals, Proceedings of the IEEE, vol. 80, No. 4 (Apr. 1992).

Boualem Boashash, Note on the Use of the Wigner Distribution for Time-Frequency Signal Analysis, IEEE Transactions on Acoustics, Speech, and Signal Processing, vol. 36, No. 9 (Sep. 1988).

Business Wire, "Mallinckrodt Announces the Nellcor N-395 Pulse Oximeter With Oxismart XL and SatSeconds," Oct. 7, 1999.

Edward Bedrosian, The Analytic Signal Representation of Modulating Waveforms (1962).

European Patent Office Official Communication pursuant to Article 96(2) EPC in Application No. 01 946 090.6-2201 dated Jun. 18, 2007 in 6 pages.

Hanzo et al., "A Portable Multimedia Communicator Scheme", Multimedia Technologies and Future Applications: Proceedings of the IEEE International Symposium (1994).

Maciej Niedzwiecki et al., "Smoothing of Discontinuous Signals: The Competitive Approach," IEEE Transactions on Signal Processing, vol. 43, No. 1 Jan. 1995, pp. 1-13.

Office Action issued in Ex Parte Reexamination U.S. Appl. No. 90/012,532 on Apr. 30, 2013.

Rusch, "Master's Thesis," Graduate School University of South Florida, Tampa, Florida (Dec. 1994).

Scharf, "Optimization of Portable Pulse Oximetry Through Fourier Analysis" USF Department of Anesthesiology, USF Department of Electrical Engineering (1993).

Scharf, "Pulse Oximetry Through Spectral Analysis", University of Southern Florida Department of Anesthesiology, University of South Florida Center for Microelectronics Research (1993).

Steven W. Smith, The Scientist and Engineer's Guide to Digital Signal Processing, § 8 (1st ed. 1997).

U.S. Appl. No. 90/012,532, filed Sep. 13, 2012, requesting ex parte reexamination of U.S. Pat. No. 7,499,835, including accompanying Reexam Request, claim charts, and other documentation filed under 37 C.F.R. § 1.510 and 35 U.S.C. § 302.

V. Ya. Volkov, "Enhancing the Reliability and Accuracy of Pulse Oximetry with a Built-In Expert System," Biomedical Engineering, vol. 27, No. 3 (May-Jun. 1993) (translated from Russian).

V. Ya. Volkov, "Principles and Algroithms for Determining Blood Oxygenation Level by Pulse Oximetry," Biomedical Engineering, vol. 27, No. 1 (Jan.-Feb. 1993) (translated from Russian).

Wukitsch, et al., "Knowing Your Monitoring Equipment," Journal of Clinical Monitoring, vol. 4, No. 4 (Oct. 1998).

(56) References Cited

OTHER PUBLICATIONS

U.S. Appl. No. 90/012,403, filed Jul. 23, 2012, requesting ex parte reexamination of U.S. Pat. No. 6,263,222, including accompanying Reexam Request, claim charts, and other documentation filed under 37 C.F.R. § 1.510 and 35 U.S.C. § 302.
U.S. Appl. No. 90/012,409, filed Aug. 17, 2012, requesting ex parte reexamination of U.S. Pat. No. 6.699,194, including accompanying Reexam Request, claim charts, and other documentation filed under 37 C.F.R. § 1.510 and 35 U.S.C. § 302.
U.S. Appl. No. 90/012,463, filed Sep. 5, 2012, requesting ex parte reexamination of of U.S. Pat. No. 7,215,984, including accompanying Reexam Request, claim charts, and other documentation filed under 37 C.F.R. § 1.510 and 35 U.S.C. § 302.
U.S. Appl. No. 90/012,534, filed Sep. 13, 2012, requesting ex parte reexamination of U.S. Pat. No. 7,962,188, including accompanying Reexam Request, claim charts, and other documentation filed under 37 C.F.R. § 1.510 and 35 U.S.C. § 302.
U.S. Appl. No. 90/012,538, filed Sep. 13, 2012, requesting ex parte reexamination of U.S. Pat. No. 7,377,899, including accompanying Reexam Request, claim charts, and other documentation filed under 37 C.F.R. § 1.510 and 35 U.S.C. § 302.
U.S. Appl. No. 90/012,541, filed Sep. 13, 2012, requesting ex parte reexamination of U.S. Pat. No. 7,899,507, including accompanying Reexam Request, claim charts, and other documentation filed under 37 C.F.R. § 1.510 and 35 U.S.C. § 302.
U.S. Appl. No. 90/012,542, filed Sep. 13, 2012, requesting ex parte reexamination of U.S. Pat. No. 8,180,420, including accompanying Reexam Request, claim charts, and other documentation filed under 37 C.F.R. § 1.510 and 35 U.S.C. § 302.
U.S. Appl. No. 90/012,543, filed Sep. 13, 2012, requesting ex parte reexamination of U.S. Pat. No. 6,850,787, including accompanying Reexam Request, claim charts, and other documentation filed under 37 C.F.R. § 1.510 and 35 U.S.C. § 302.
U.S. Appl. No. 90/012,546, filed Sep. 13, 2012, requesting ex parte reexamination of U.S. Pat. No. 7,438,683, including accompanying Reexam Request, claim charts, and other documentation filed under 37 C.F.R. § 1.510 and 35 U.S.C. § 302.
U.S. Appl. No. 90/012,548, filed Sep. 13, 2012, requesting ex parte reexamination of U.S. Pat. No. 7,880,606, including accompanying Reexam Request, claim charts, and other documentation filed under 37 C.F.R. § 1.510 and 35 U.S.C. § 302.
U.S. Appl. No. 90/012,.551, filed Sep. 13, 2012, requesting ex parte reexamination of U.S. Pat. No. 6,970,792, including accompanying Reexam Request, claim charts, and other documentation filed under 37 C.F.R. § 1.510 and 35 U.S.C. § 302.
U.S. Appl. No. 90/012,.553, filed Sep. 13, 2012, requesting ex parte reexamination of U.S. Pat. No. 7,024,233, including accompanying Reexam Request, claim charts, and other documentation filed under 37 C.F.R. § 1.510 and 35 U.S.C. § 302.
U.S. Appl. No. 90/012.555, filed Sep. 13, 2012, requesting ex parte reexamination of U.S. Pat. No. 7,440,787, including accompanying Reexam Request, claim charts, and other documentation filed under 37 C.F.R. § 1.510 and 35 U.S.C. § 302.
U.S. Appl. No. 90/012,557, filed Sep. 13, 2012, requesting ex parte reexamination of U.S. Pat. No. 8,150,487, including accompanying Reexam Request, claim charts, and other documentation filed under 37 C.F.R. § 1.510 and 35 U.S.C. § 302.
U.S. Appl. No. 90/012,559, filed Sep. 13, 2012, requesting ex parte reexamination of U.S. Pat. No. 8,190,223, including accompanying Reexam Request, claim charts, and other documentation filed under 37 C.F.R. § 1.510 and 35 U.S.C. § 302.
U.S. Appl. No. 90/012,561, filed Sep. 14, 2012, requesting ex parte reexamination of U.S. Pat. No. 8,019400, including accompanying Reexam Request, claim charts, and other documentation filed under 37 C.F.R. § 1.510 and 35 U.S.C. § 302.
U.S. Appl. No. 90/012,562, filed Sep. 14, 2012 requesting ex parte reexamination of U.S. Pat. No. 6,463,311, including accompanying Reexam Request, claim charts, and other documentation filed under 37 C.F.R. § 1.510 and 35 U.S.C. § 302.
U.S. Appl. No. 90/012,566, filed Sep. 14, 2012, requesting ex parte reexamination of U.S. Pat. No. 7,530,955, including accompanying Reexam Request, claim charts, and other documentation filed under 37 C.F.R. § 1.510 and 35 U.S.C. § 302.
U.S. Appl. No. 90/012,567, filed Sep. 14, 2012, requesting ex parte reexamination of U.S. Pat. No. 6,684,090, including accompanying Reexam Request, claim charts, and other documentation filed under 37 C.F.R. § 1.510 and 35 U.S.C. § 302.
U.S. Appl. No. 90/012,568, filed Sep. 14, 2012, requesting ex parte reexamination of U.S. Pat. No. 8,128,572, including accompanying Reexam Request, claim charts, and other documentation filed under 37 C.F.R. § 1.510 and 35 U.S.C. § 302.
U.S. Appl. No. 90/012,699, filed Oct. 4, 2012, requesting ex parte reexamination of U.S. Pat. No. 6,002,952, including accompanying Reexam Request, claim charts, and other documentation filed under 37 C.F.R. § 1.510 and 35 U.S.C. § 302.
U.S. Appl. No. 95/002,183, filed Sep. 12, 2012, requesting inter partes reexamination of U.S. Pat. No. 7,530,955, including accompanying Reexam Request, claim charts, and other documentation filed under 37 C.F.R. § 1.913 and 35 U.S.C. § 311.
Declaration of Perry D. Oldham in Support of Masimo Opposition to Defendant's Motion for Summary Judgment of Invalidity and Noninfringement of U.S. Pat. No. 7,215,984, vol. 1, Doc. 556, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012. (Redacted).
Declaration of Perry D. Oldham in Support of Masimo's Opposition to Defendant's Motion for Summary Judgment of Invalidity and Noninfringement of U.S. Pat. No. 7,215,984, vol. 2, Doc. 558, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012. (Redacted).
Masimo Corporation's Answering Brief in Opposition to Defendant's Motion for Summary Judgment of Invalidity and Noninfringement of U.S. Patent. No. 7,215,984, Doc. 555, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012. (Redacted).
Philip's Opening Brief in Support of Defendant's Motion for Summary Judgment of Invalidity and Nonigringement of U.S. Pat. No. 7,215,984, Doc. 442, *Masimo Corporation v. Philips Electronics North America Corporation and Philips Medizin Systeme Böblingen GMBH*, (District of Delaware, Case No. 1:09-cv-00080 (LPS/MPT) dated Aug. 21, 2012. (Redacted).
Philip Defendant's Motion for Summary Judgment of Invalidity and Noninfringement of U.S. Pat. No. 7,215,984, Doc. 394, *Masimo Corporation v. Philips Electronics North America Corporation and Philips Medizin Systeme Böblingen GMBH*, (District of Delaware, Case No. 1:09-cv-00080 (LPS/MPT) dated Aug. 14, 2012.
Reply Brief in Support of Defendants' Motion for Summary Judgment of invalidity and Noninfringement of U.S. Patent. No. 7,216,984, Doc. 609, *Masimo Corporation v. Philips Electronics North America Corporation and Philips Medizin Systeme Böblingen GMBH*, (District of Delaware, Case No. 1:09-cv-00080 (LPS/MPT) dated Oct. 26, 2012. (Redacted).
Declaration of Gail Baura, Ph.D. In Support of Masimo's Opposition to Defendant's Motion for Summary Judgment of Invalidity of U.S. Pat. No. 7,215,984, Doc. 561, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012. (Redacted).
Declaration of Gail Baura, Ph.D. in Support of Masimo's Opposition to Defendant's Motion for Summary Judgment of Invalidity of U.S. Pat. No. 5,632,272, Doc. 554, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012. (Redacted).
Declaration of Perry D. Oldham in Support of Masimo Opposition to Defendant's Motion for Summary Judgment of Invalidity of U.S. Pat. No. 5,632,272, Doc. 553, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012. (Redacted).

(56) References Cited

OTHER PUBLICATIONS

Masimo Corporation's Answering Brief in Opposition to Defendant's Motion for Summary Judgment of Invalidity and Noninfringement of U.S. Pat. No. 5,632,272, Doc. 552, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012. (Redacted).
Opening Brief in Support of Defendants' Motion for Summary Judgment of Invalidity and Noninfringement of U.S. Pat. No. 5,632,272, Doc. 444, *Masimo Corporation v. Philips Electronics North America Corporation and Philips Medizin Systeme Böblingen GMBH*, (District of Delaware, Case No. 1:09-cv-00080 (LPS/MPT) dated Aug. 21, 2012. (Redacted).
Defendants' Motion for Summary Judgment of Invalidity and Noninfringement of U.S. Pat. No. 5,632,272, Doc. 402, *Masimo Corporation v. Philips Electronics North America Corporation and Philips Medizin Systeme Böblingen GMBH*, (District of Delaware, Case No. 1:09-cv-00080 (LPS/MPT) dated Aug. 14, 2012.
Reply Brief in Support of Defendants' Motion for Summary Judgment of Invalidity and Noninfringement of U.S. Pat. No. 5,632,272, Doc. 614, *Masimo Corporation v. Philips Electronics North America Corporation and Philips Medizin Systeme Böblingen GMBH*, (District of Delaware, Case No. 1:09-cv-00080 (LPS/MPT) dated Oct. 26, 2012 (Redacted).
Declaration of Mohammed K. Diab in Support of Masimo's Oppositions to Defendants' Motions for Summary Judgment of Invalidity and Noninfringement of U.S. Pat. No. 5,632,272 and 7,215,984, Doc. 563, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012 (Redacted).
Declaration of Perry D. Oldham in Support of Masimo's Opposition to Defendant's Motion for Summary Judgment of Invalidity of U.S. Pat. No. 6,263,222, Doc. 550, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012 (Redacted).
Masimo Corporation's Answering Brief in Opposition to Defendants' Motion for Summary Judgment of Invalidity of U.S. Pat. No. 6,263,222, Doc. 549, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012 (Redacted).
Philips' Opening Brief in Support of Defendants' Motion for Summary Judgment of Invalidity of U.S. Pat. No. 6,263,222, Doc. 413, *Masimo Corporation v. Philips Electronics North America Corporation and Philips Medizin Systeme Böblingen GMBH*, (District of Delaware, Case No. 1:09-cv-00080 (LPS/MPT) dated Aug. 14, 2012.
Defendants' Motion for Summary Judgment of Invalidity of U.S. Pat. No. 6,263,222, Doc. 410, *Masimo Corporation v. Philips Electronics North America Corporation and Philips Medizin Systeme Böblingen GMBH*, (District of Delaware, Case No. 1:09-cv-00080 (LPS/MPT) dated Aug. 14, 2012.
Reply Brief in Support of Defendants' Motion for Summary Judgment of Invalidity of U.S. Pat. No. 6,263,222, Doc. 613, *Masimo Corporation v. Philips Electronics North America Corporation and Philips Medizin Systeme Böblingen GMBH*, (District of Delaware, Case No. 1:09-cv-00080 (LPS/MPT) dated oCT. 26, 2012 (Redacted).
Declaration of Gail Baura, Ph.D. In Support of Masimo's Opposition to Defendant's Motion for Summary Judgment of Invalidity of U.S. Pat. No. 6,263,222, Doc. 551, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012. (Redacted).
Declaration of Gail Baura, Ph.D. In Support of Masimo's Opposition to Defendant's Motion for Summary Judgment of Invalidity of U.S. Pat. No. 6,699,194, Doc. 508, *Masimo Corporation v. Philips Electronics North America Corporation and Philips Medizin Systeme Böblingen GMBH*, (District of Delaware, Case No. 1:09-cv-00080 (LPS/MPT) dated Sep. 21, 2012.
Opening Brief in Support of Defendants' Motion for Summary Judgment of Invalidity of U.S. Pat. No. 6,699,194, Doc. 445, *Masimo Corporation v. Philips Electronics North America Corporation and Philips Medizin Systeme Böblingen GMBH*, (District of Delaware, Case No. 1:09-cv-00080 (LPS/MPT) dated Aug. 21, 2012. (Redacted).
Defendants' Motion for Summary Judgment of Invalidity of U.S. Pat. No. 6,699,194, Doc. 406, *Masimo Corporation v. Philips Electronics North America Corporation and Philips Medizin Systeme Böblingen GMBH*, (District of Delaware, Case No. 1:09-cv-00080 (LPS/MPT) dated Aug. 14, 2012.
Reply Brief in Support of Defendants' Motion for Summary Judgment of Invalidity of U.S. Pat. No. 6,699,194, Doc. 610, *Masimo Corporation v. Philips Electronics North America Corporation and Philips Medizin Systeme Böblingen GMBH*, (District of Delaware, Case No. 1:09-cv-00080 (LPS/MPT) dated Oct. 26, 2012. (Redacted).
Declaration of Perry D. Oldham in Support of Masimo Opposition to Defendant's Motion for Summary Judgment of Invalidity of U.S. Pat. No. 6,699,194, Doc. 548, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012. (Redacted).
Philips' Response to Masimo Corporation's Objections to the Report and Recommendation Regarding Claim Construction, Doc. 230, *Masimo Corporation v. Philips Electronics North America Corporation and Philips Medizin Systeme Böblingen GMBH*, (District of Delaware, Case No. 1:09-cv-00080 (LPS/MPT) dated Mar. 24, 2011.
Masimo Corporation's Objections to the Report and Recommendation Regarding Claim Construction, Doc. 219, *Masimo Corporation v. Philips Electronics North America Corporation and Philips Medizin Systeme Böblingen GMBH*, (District of Delaware, Case No. 1:09-cv-00080 (LPS/MPT) dated Mar. 8, 2011.
Defendants' Objections to Magistrate Judge Thynge's Report and Recommendation Regarding Claim Construction, Doc. 218, *Masimo Corporation v. Philips Electronics North America Corporation and Philips Medizin Systeme Böblingen GMBH*, (District of Delaware, Case No. 1:09-cv-00080 (LPS/MPT) dated Mar. 7, 2011.
Report and Recommendation Regarding Claim Construction, Doc. 210, *Masimo Corporation v. Philips Electronics North America Corporation and Philips Medizin Systeme Böblingen GMBH*, (District of Delaware, Case No. 1:09-cv-00080 (LPS/MPT) dated Feb. 18, 2011.
Memorandum Order Adopting Report and Recommendation Regarding Claim Construction, Doc. 319, *Masimo Corporation v. Philips Electronics North America Corporation and Philips Medizin Systeme Böblingen GMBH*, (District of Delaware, Case No. 1:09-cv-00080 (LPS/MPT) dated Jan. 17, 2011.
Masimo Corporation's Response to Defendants' Objections to the Report and Recommendation Regarding Claim Construction, Doc. 232, *Masimo Corporation v. Philips Electronics North America Corporation and Philips Medizin Systeme Böblingen GMBH*, (District of Delaware, Case No. 1:09-cv-00080 (LPS/MPT) dated Mar. 24, 2011.
Supplemental Expert Report of Dr. Robert Stone Regarding the invalidity of Masimo's Patents-in-Suit (U.S. Pat. No. 5,632,272, U.S. Pat. No. 6,263,222, U.S. Pat. No. 7,215,984, and U.S. Pat. No. 6,699,194, *Masimo Corporation v. Philips Electronics North America Corporation and Philips Medizin Systeme Böblingen GMBH*, (District of Delaware, Case No. 1:09-cv-00080 (LPS/MPT) dated Mar. 18, 2012.
Appendixes for Expert Report of Dr. Robert Stone Regarding the invalidity of Masimo's Patents-in-Suit (U.S. Pat. No. 5,632,272, U.S. Pat. No. 6,263,222, U.S. Pat. No. 7,215,984, and U.S. Pat. No. 6,699,194, *Masimo Corporation v. Philips Electronics North America Corporation and Philips Medizin Systeme Böblingen GMBH*, (District of Delaware, Case No. 1:09-cv-00080 (LPS/MPT) dated Mar. 7, 2012.
Expert Report of Dr. Robert Stone Regarding the invalidity of Masimo's Patents-in-Suit (U.S. Pat. No. 5,632,272, U.S. Pat. No. 6,263,222, U.S. Pat. No. 7,215,984, and U.S. Pat. No. 6,699,194, *Masimo Corporation v. Philips Electronics North America Corporation and Philips Medizin Systeme Böblingen GMBH*, (District of Delaware, Case No. 1:09-cv-00080 (LPS/MPT) dated Mar. 7, 2012.

(56) References Cited

OTHER PUBLICATIONS

Second Amended Complaint for Patent Infringement, Doc. 42, *Masimo Corporation v. Philips Electronics North America Corporation and Philips Medizin Systeme Böblingen GMBH*, (District of Delaware, Case No. 1:09-cv-00080 (LPS/MPT) dated Apr. 25, 2012.

Masimo's Answer to Philips' Counterclaims, Doc. 28, *Masimo Corporation v. Philips Electronics North America Corporation and Philips Medizin Systeme Böblingen GMBH*, (District of Delaware, Case No. 1:09-cv-00080 (LPS/MPT) dated Dec. 30, 2011.

Defendants' Answer and Philips Electronics North America Corp.'s Counterclaims to Masimo's First Amended Complaint, Doc. 11, *Masimo Corporation v. Philips Electronics North America Corporation and Philips Medizin Systeme Böblingen GMBH*, (District of Delaware, Case No. 1:09-cv-00080 (LPS/MPT) dated Nov. 7, 2011.

Masimo's Answer to Philips' Counterclaims to Masimo's Second Amended Complaint, Doc. 358, *Masimo Corporation v. Philips Electronics North America Corporation and Philips Medizin Systeme Böblingen GMBH*, (District of Delaware, Case No. 1:09-cv-00080 (LPS/MPT) dated Jun. 4, 2012.

Defendants' Answer and Philips Electronics North America Corp.'s Counterclaims to Masimo's Second Amended Complaint, Doc. 43, *Masimo Corporation v. Philips Electronics North America Corporation and Philips Medizin Systeme Böblingen GMBH*, (District of Delaware, Case No. 1:09-cv-00080 (LPS/MPT) dated May 11, 2012.

Office Action issued in Ex Parte Reexamination in Application No. 90/012,532 dated Apr. 30, 2013.

Notice of Intent to Issue Ex Parte Reexamination Certificate in Application No. 90/012,532, dated Sep. 23, 2013.

Reexamination Certificate in in Application No. 90/012,532, dated Dec. 19, 2013.

VARIABLE INDICATION ESTIMATOR

INCORPORATION BY REFERENCE TO ANY PRIORITY APPLICATIONS

Any and all applications, if any, for which a foreign or domestic priority claim can be identified in the Application Data Sheet of the present application is hereby incorporated by reference under 37 CFR 1.57.

FIELD OF THE INVENTION

The present invention is directed to the field of signal processing, and, more particularly, is directed to systems and methods for determining a representative estimate output value for a window of input data.

BACKGROUND OF THE INVENTION

Digital signal processing techniques are frequently employed to enhance a desired signal in a wide variety of applications, such as health care, communications and avionics, to name a few. Signal enhancement includes smoothing, filtering and prediction. These processing techniques each operate on a block of input signal values, such as, for example, a window of input signal values, in order to estimate the signal at a specific point in time. FIG. 1 illustrates that smoothing, filtering and prediction can be distinguished by the time at which an output value is generated relative to input values. Shown in FIG. 1 is a time axis 100 and a block 101 of input signal values depicted in this example as occurring within a time window between points $t^{min}$ and $t_{max}$. Specifically, the block 101 includes a set of discrete input values $\{v_i; i=1, 2, \ldots n\}$ occurring at a corresponding set of time points $\{t_i; i=1, 2, \ldots n\}$. A smoother operates on the block 101 of input values to estimate the signal at a time point, $t_s$ 102 between $t^{min}$ and $t^{max}$. That is, a smoother generates an output value based upon input values occurring before and after the output value. A filter operates on the block 101 of input values to estimate the signal at a time $t_f$ 104, corresponding to the most recently occurring input value in the block 101. That is, a filter generates a forward filtered output value at the time $t_f$ based upon input values occurring at, and immediately before, the output value. A filter also operates on the block 101 to estimate the signal at a time $t_b$ 105 at the beginning of the block 101 to generate a backward filtered value. A forward predictor operates on the block of input values 101 to estimate the signal at time $t_{pf}$ 106, which is beyond the most recently occurring value in the block 101. That is, a forward predictor generates a forward predicted output value based upon input values occurring prior to the output value. A backward predictor operates on the block 101 of input values to estimate the signal at time $t_{pb}$ 108, which is before the earliest occurring value in the block 101. That is, a backward predictor generates a backward predicted output value based upon input values occurring after the output value.

SUMMARY OF THE INVENTION

A common smoothing technique uses an average to fit a constant, $v^A$, to a set of data values, $\{v_i; i=1, 2, \ldots, n\}$:

$$v^A = \frac{1}{n} \cdot \sum_{i=1}^{n} v_i \tag{1}$$

A generalized form of equation (1) is the weighted average $$v^{WA} = \frac{\sum_{i=1}^{n} w_i \cdot v_i}{\sum_{i=1}^{n} w_i} \tag{2}$$

Here, each value, $v_i$, is scaled by a weight, $w_i$, before averaging. This allows data values to be emphasized and de-emphasized relative to each other. If the data relates to an input signal, for example, values occurring during periods of low signal confidence can be given a lower weight and values occurring during periods of high signal confidence can be given a higher weight.

FIG. 2A illustrates the output of a constant mode averager, which utilizes the weighted average of equation (2) to process a discrete input signal, $\{v_i; i$ an integer$\}$ 110. The input signal 110 may be, for example, a desired signal corrupted by noise or a signal having superfluous features. The constant mode averager suppresses the noise and unwanted features, as described with respect to FIG. 5, below. A first time-window 132 defines a first set, $\{v_i; i=1, 2, \ldots, n\}$, of signal values, which are averaged together to produce a first output value, $z_1$ 122. A second time-window 134, shifted from the previous window 132, defines a second set $\{v_i; i=2, 3, \ldots, n+1\}$ of signal values, which are also averaged together to produce a second output value $z_2$ 124. In this manner, a discrete output signal, $\{z_j; j$ an integer$\}$ 120 is generated from a moving weighted average of a discrete input signal $\{v_i; i$ an integer$\}$ 110, where:

$$z_j = \sum_{i=j}^{n+j-1} w_i v_i \bigg/ \sum_{i=j}^{n+j-1} w_i \tag{3}$$

A common filtering technique computes a linear fit to a set of data values, $\{v_i; i=1, 2, \ldots, n\}$:

$$\hat{v}_i = \alpha \cdot t_i + \beta \tag{4}$$

where $\alpha$ and $\beta$ are constants and $t_i$ is the time of occurrence of the $i^{th}$ value. FIG. 2B illustrates the output of a linear mode averager, which uses the linear fit of equation (4) to process a discrete input signal, $\{v_i; i$ an integer$\}$ 110. The input signal 110 may be, for example, a desired signal with important features corrupted by noise. The linear mode averager reduces the noise but tracks the important features, as described with respect to FIG. 6 below. A first time-window 132 defines a first set, $\{v_i; i=1, 2, \ldots, n\}$, of signal values. A linear fit to these n values is a first line 240, and the value along this line at $\max\{t_1, t_2, \ldots, t_n\}$ is equal to a first output value, $z_1$ 222. A second time-window 134 shifted from the previous window 132 defines a second set, $\{v_i; i=2, 3, \ldots, n+1\}$, of signal values. A linear fit to these n values is a second line 250, and the value along this line at $\max\{t_2, t_3, \ldots, t_{n+1}\}$ is equal to a second output value, $z_2$ 224. In this manner, a discrete output signal, $\{z_j; j$ an integer$\}$ 220 is generated from a moving linear fit of a discrete input signal $\{v_i; i$ an integer$\}$, where:

$$z_j = \alpha_j \cdot t_{n+j-1}^{MAX} + \beta_j \tag{5a}$$

$$t_{n+j-1}^{MAX} = \max\{t_j, t_{j+1}, L, t_{n+j-1}\} \tag{5b}$$

In general, the time windows shown in FIGS. 2A-2B may be shifted from each other by more than one input value, and values within each time window may be skipped, i.e., not included in the average. Further, the $t_i$'s may not be in increasing or decreasing order or uniformly distributed, and successive time windows may be of different sizes. Also, although the discussion herein refers to signal values as the dependent variable and to time as the independent variable to facilitate disclosure of the present invention, the concepts involved are equally applicable where the variables are other than signal values and time. For example, an independent variable could be a spatial dimension and a dependent variable could be an image value.

The linear mode averager described with respect to FIG. 2B can utilize a "best" linear fit to the input signal, calculated by minimizing the mean-squared error between the linear fit and the input signal. A weighted mean-squared error can be described utilizing equation (4) as:

$$\varepsilon(\alpha, \beta) = \sum_{i=1}^{n} w_i (v_i - \hat{v}_i)^2 \bigg/ \sum_{i=1}^{n} w_i \tag{6a}$$

$$\varepsilon(\alpha, \beta) = \sum_{i=1}^{n} w_i [v_i - (\alpha \cdot t_i + \beta)]^2 \bigg/ \sum_{i=1}^{n} w_i \tag{6b}$$

Conventionally, the least-mean-squared (LMS) error is calculated by setting the partial derivatives of equation (6b) with respect to $\alpha$ and $\beta$ to zero:

$$\frac{\partial}{\partial \alpha} \varepsilon(\alpha, \beta) = 0 \tag{7a}$$

$$\frac{\partial}{\partial \beta} \varepsilon(\alpha, \beta) = 0 \tag{7b}$$

Substituting equation (6b) into equation (7b) and taking the derivative yields:

$$-2 \sum_{i=1}^{n} w_i [v_i - (\alpha \cdot t_i + \beta)] \bigg/ \sum_{i=1}^{n} w_i = 0 \tag{8}$$

Solving equation (8) for $\beta$ and substituting the expression of equation (2) yields:

$$\beta = \frac{\sum_{i=1}^{n} w_i \cdot v_i}{\sum_{i=1}^{n} w_i} - \alpha \frac{\sum_{i=1}^{n} w_i \cdot t_i}{\sum_{i=1}^{n} w_i} \tag{9a}$$

$$\beta = v^{WA} - \alpha \cdot t^{WA} \tag{9b}$$

where the weighted average time, $t^{WA}$, is defined as:

$$t^{WA} = \frac{\sum_{i=1}^{n} w_i \cdot t_i}{\sum_{i=1}^{n} w_i} \tag{10}$$

Substituting equation (9b) into equation (4) gives:

$$\hat{v}_i = \alpha(t_i - t^{WA}) + v^{WA} \tag{11}$$

Substituting equation (11) into equation (6a) and rearranging terms results in:

$$\varepsilon(\alpha, \beta) = \sum_{i=1}^{n} w_i [(v_i - v^{WA}) - \alpha \cdot (t_i - t^{WA})]^2 \bigg/ \sum_{i=1}^{n} w_i \tag{12}$$

Changing variables in equation (12) gives:

$$\varepsilon(\alpha, \beta) = \sum_{i=1}^{n} w_i (v_i' - \alpha \cdot t_i')^2 \bigg/ \sum_{i=1}^{n} w_i \tag{13}$$

where:

$$v_i' = v_i - v^{WA} \tag{14a}$$

$$t_i' = t_i - t^{WA} \tag{14b}$$

Substituting equation (13) into equation (7a) and taking the derivative yields $$-2 \sum_{i=1}^{n} w_i t_i' (v_i' - \alpha \cdot t_i') \bigg/ \sum_{i=1}^{n} w_i = 0 \tag{15}$$

Solving equation (15) for $\alpha$ gives:

$$\alpha = \frac{\sum_{i=1}^{n} w_i v_i' t_i' \bigg/ \sum_{i=1}^{n} w_i}{\sum_{i=1}^{n} w_i t_i'^2 \bigg/ \sum_{i=1}^{n} w_i} \tag{16}$$

Substituting equations (14a, b) into equation (16) results in:

$$\alpha = \frac{\sum_{i=1}^{n} w_i (v_i - v^{WA})(t_i - t^{WA}) \bigg/ \sum_{i=1}^{n} w_i}{\sum_{i=1}^{n} w_i (t_i - t^{WA})^2 \bigg/ \sum_{i=1}^{n} w_i} \tag{17a}$$

$$\alpha = \frac{\sigma_{vt}^2}{\sigma_{tt}^2} \tag{17b}$$

where:

$$\sigma_{vt}^2 = \sum_{i=1}^{n} w_i (v_i - v^{WA})(t_i - t^{WA}) \bigg/ \sum_{i=1}^{n} w_i \tag{18a}$$

$$\sigma_{tt}^2 = \sum_{i=1}^{n} w_i (t_i - t^{WA})^2 \bigg/ \sum_{i=1}^{n} w_i \tag{18b}$$

Finally, substituting equation (17b) into equation (11) provides the equation for the least-mean-square (LMS) linear fit to $\{v_i; i=1, 2, \ldots, n\}$:

$$\hat{v}_i = \frac{\sigma_{vt}^2}{\sigma_{tt}^2}(t_i - t^{WA}) + v^{WA} \tag{19}$$

FIG. 3 provides one comparison between the constant mode averager, described above with respect to FIG. 2A and equation (2), and the linear mode averager, described above with respect to FIG. 2B and equation (19). Shown in FIG. 3 are input signal values $\{v_i; i=1, 2, \ldots, n\}$ 310. The constant mode averager calculates a constant 320 for these values 310, which is equal to $v^{WA}$, the weighted average of the input values $v_i$. Thus, the constant mode averager output 340 has a value $v^{WA}$. For comparison to the linear mode averager, the constant mode averager output can be conceptualized as an estimate of the input values 310 along a linear fit 350, evaluated at time $t^{WA}$. The linear mode averager may be thought of as calculating a LMS linear fit, $\hat{v}_i$ 330 to the input signal values, $v_i$ 310. The linear mode averager output 350 has a value, $v^{WLA}$. The linear mode averager output is an estimate of the input values 310 along the linear fit 330, described by equation (19), evaluated at an index i such that $t_i = t^{MAX}$:

$$v^{WLA} = \frac{\sigma_{vt}^2}{\sigma_{tt}^2}(t^{MAX} - t^{WA}) + v^{WA} \qquad (20)$$

where:

$$t^{MAX} = \max\{t_1, t_2, L, t_n\} \qquad (21)$$

As illustrated by FIG. 3, unlike the constant mode averager, the linear mode averager is sensitive to the input signal trend. That is, the constant mode averager provides a constant fit to the input values, whereas the linear mode averager provides a linear fit to the input values that corresponds to the input value trend. As a result, the output of the linear mode averager output responds faster to changes in the input signal than does the output of the constant mode averager. The time lag or delay between the output of the constant mode averager and the output of the linear mode averager can be visualized by comparing the time difference 360 between the constant mode averager output value 340 and the linear mode averager output value 350.

FIGS. 4-6 illustrate further comparisons between the constant mode averager and the linear mode averager. FIG. 4 depicts a noise-corrupted input signal 410, which increases in frequency with time. FIGS. 5-6 depict the corresponding noise-free signal 400. FIG. 5 also depicts the constant mode averager output 500 in response to the input signal 410, with the noise-free signal 400 shown for reference. FIG. 6 depicts the linear mode averager output 600 in response to the input signal 410, with the noise-free signal 400 also shown for reference. As shown in FIG. 5, the constant mode averager output 500 suppresses noise from the input signal 410 (FIG. 4) but displays increasing time lag and amplitude deviation from the input signal 400 as frequency increases. As shown in FIG. 6, the linear mode averager output 600 tends to track the input signal 400 but also tracks a portion of the noise on the input signal 410.

FIGS. 4-6 suggest that it would be advantageous to have an averager that has variable characteristics between those of the linear mode averager and those of the constant mode averager, depending on signal confidence. Specifically, it would be advantageous to have a variable mode averager that can be adjusted to track input signal features with a minimal output time lag when signal confidence is high and yet adjusted to smooth an input signal when signal confidence is low. Further, it would be advantageous to have a variable mode averager that can be adjusted so as not to track superfluous input signal features regardless of signal confidence.

One aspect of the present invention is a variable mode averager having a buffer that stores weighted input values. A mode input specifies a time value relative to the input values. A processor is coupled to the buffer, and the processor is configured to provide an estimate of the input values that corresponds to the time value. In a particular embodiment, the mode input is adjustable so that the estimate varies between that of a smoother and that of a forward predictor of the input values. In another embodiment, the mode input is adjustable so that the estimate varies between that of a smoother and that of a filter of the input values. In yet another embodiment, the mode input is adjustable so that the estimate varies between that of an average of the input values and that of a filter of the input values. The mode input may be adjustable based upon a characteristic associated with the input values, such as a confidence level. In one variation of that embodiment, the estimate can be that of a smoother when the confidence level is low and that of a filter when the confidence level is high. The estimate may occur along a curve-fit of the input values at the time value. In one embodiment, the curve-fit is a linear LMS fit to the input values.

Another aspect of the present invention is a signal averaging method. The method includes identifying signal values and determining weights corresponding to the signal values. The method also includes computing a trend of the signal values adjusted by the weights. Further, the method includes specifying a time value relative to the signal values based upon a characteristic associated with the signal values and estimating the signal values based upon the trend evaluated at the time value. The method may also incorporate the steps of determining a confidence level associated with the signal values and specifying the time value based upon the confidence level. In one embodiment, the trend is a linear LMS fit to the signal values adjusted by the weights. In that case, the time value may generally correspond to the maximum time of the signal values when the confidence level is high and generally correspond to the weighted average time of the signal values when the confidence level is low.

Yet another aspect of the present invention is a signal averaging method having the steps of providing an input signal, setting a mode between a first mode value and a second mode value and generating an output signal from an estimate of the input signal as a function of said mode. The output signal generally smoothes the input signal when the mode is proximate the first mode value, and the output signal generally tracks the input signal when the mode is proximate the second mode value. The method may also include determining a characteristic of the input signal, where the setting step is a function of the characteristic. In one embodiment, the characteristic is a confidence level relating to the input signal. In another embodiment, the setting step incorporates the substeps of setting the mode proximate the first mode value when the confidence level is low and setting the mode proximate the second mode value when the confidence level is high. In another embodiment, the input signal is a physiological measurement and the setting step comprises setting the mode proximate the first mode value when the measurement is corrupted with noise or signal artifacts and otherwise setting the mode proximate the second mode value so that the output signal has a fast response to physiological events.

A further aspect of the present invention is a signal averager having an input means for storing signal values, an adjustment means for modifying the signal values with corresponding weights, a curve fitting means for determining a trend of the signal values, and an estimate means for generating an output value along the trend. The signal averager may further have a mode means coupled to the estimate means for variably determining a time value at which to generate the output value.

For purposes of summarizing the invention, certain aspects, advantages and novel features of the invention have been described herein. Of course, it is to be understood that not necessarily all such aspects, advantages or features will be embodied in any particular embodiment of the invention.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements. In addition, the first digit of each reference number indicates the figure in which the element first appears.

DETAILED DESCRIPTION OF THE PREFERRED EMBODIMENTS

Figure 7:
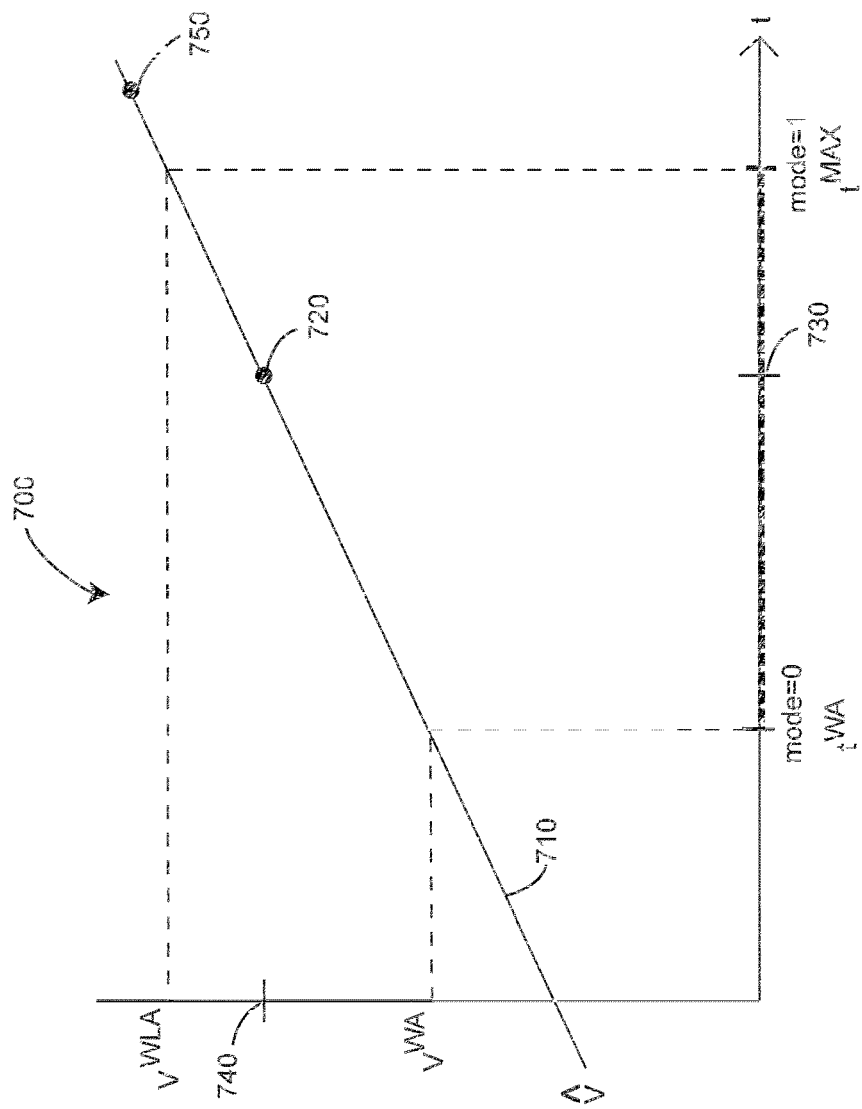
FIG. 7 is an amplitude versus time graph illustrating the characteristics of one embodiment of the variable mode averager.

FIG. 7 illustrates the output characteristics of a variable mode averager according to the present invention. The output of the variable mode averager is a mode-dependent weighted linear average (MWLA) defined as $$v^{MWLA} = \text{mode} \cdot \frac{\sigma_{vt}^2}{\sigma_{tt}^2}(t^{MAX} - t^{WA}) + v^{WA} \quad (22)$$

Equation (22) is a modified form of equation (20), which is motivated by equations (2) and (19) along with recognition of the relationships in Table 1.

TABLE 1

VARIABLE MODE AVERAGER OUTPUT

Figure 8:
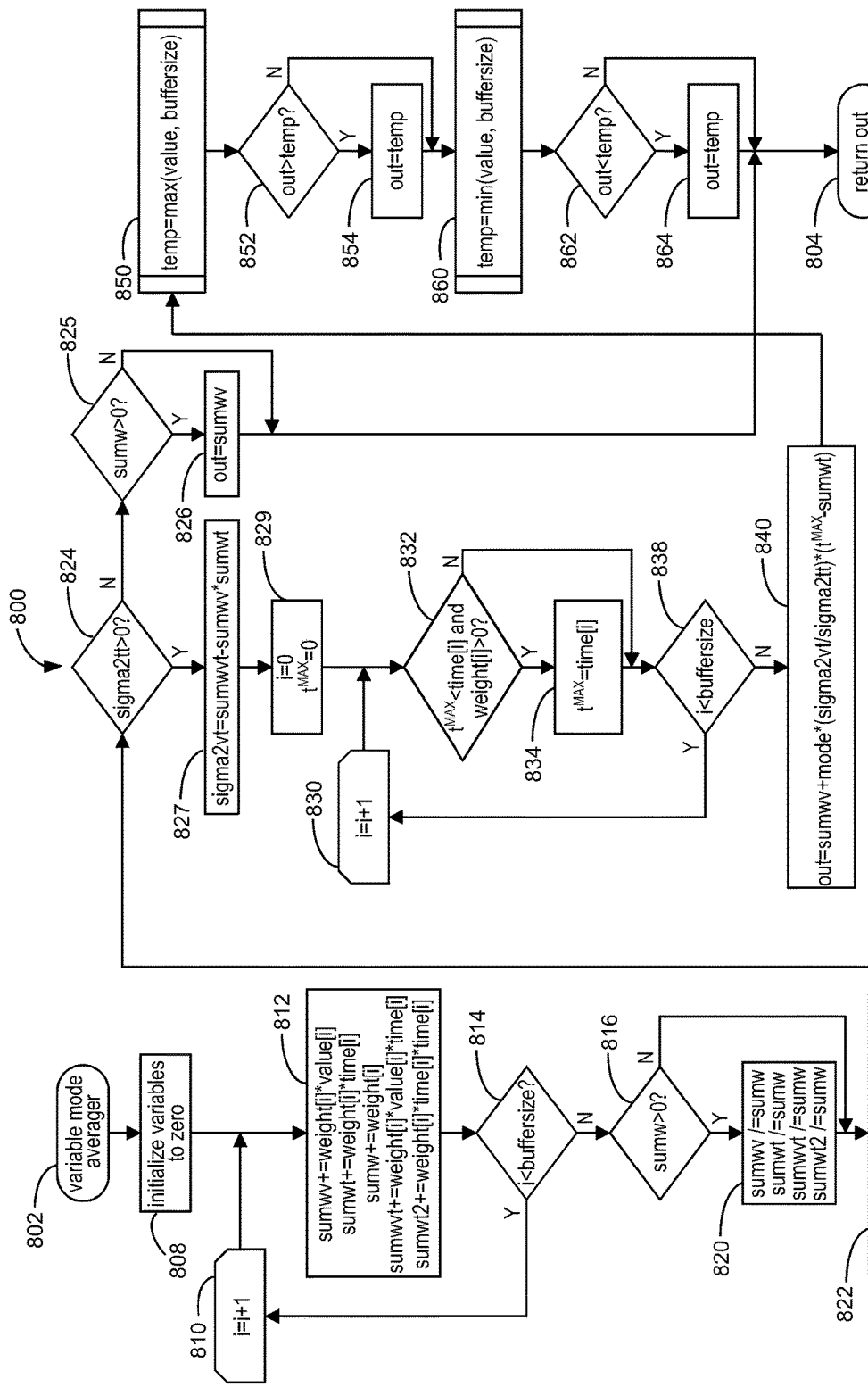
FIG. 8 is a flow chart of a variable mode averager embodiment.

| | mode = 0 | mode = 1 | any mode ≠ 0 |
|---|---|---|---|
| Processing Function | Constant Mode Averager | Linear Mode Averager | Variable Mode Averager |
| Output | $v^{WA}$ | $v^{WLA}$ | $v^{MWLA}$ |
| Defining Formula | Equation (2) | Equation (20) | Equation (22) |
| Processing Method | Weighted Average | LMS Linear Fit | FIG. 8 |

As shown in Table 1, the Variable Mode Averager in accordance with the present invention includes the constant mode averager processing function and the linear mode averager processing function, which are known processing functions. As further shown in Table 1, the Variable Mode Averager of the present invention also includes a variable mode averager processing function, which will be described below.

As shown in Table 1, if mode=0, the variable mode averager output is $v^{WA}$, the output of the constant mode averager function, which utilizes a weighted average of the input signal values. If mode=1, the variable mode averager output is $v^{WLA}$, the output of the linear mode averager function, which utilizes a LMS linear fit to the input signal values. If 0<mode<1, then the variable mode averager output is $v^{MWLA}$ and has output characteristics that are between that of the constant mode averager and the linear mode averager. In addition, if mode>1, then the variable mode averager behaves as a forward predictor.

Figure 1:
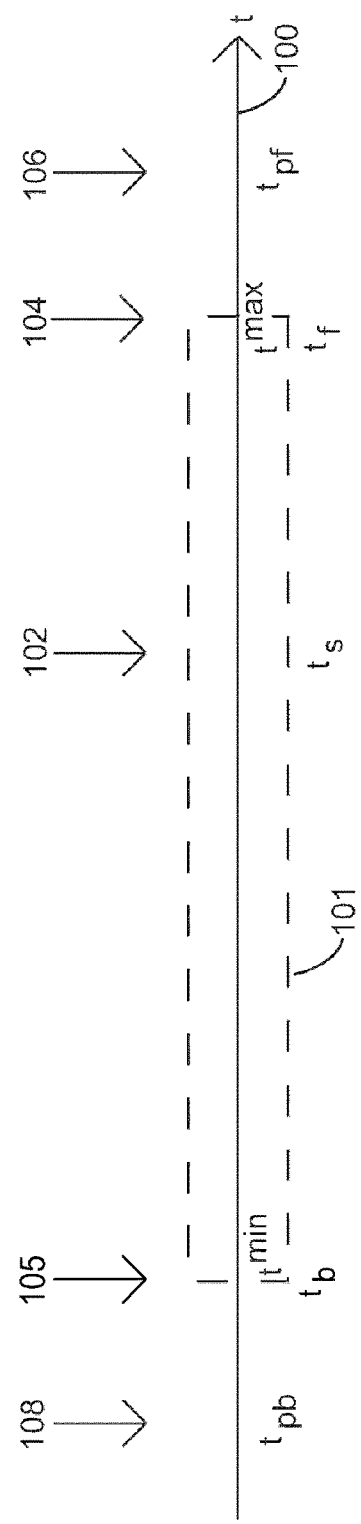
FIG. 1 is a time graph depicting the output of conventional smoother, filter and predictor signal processors.
Figure 2A:
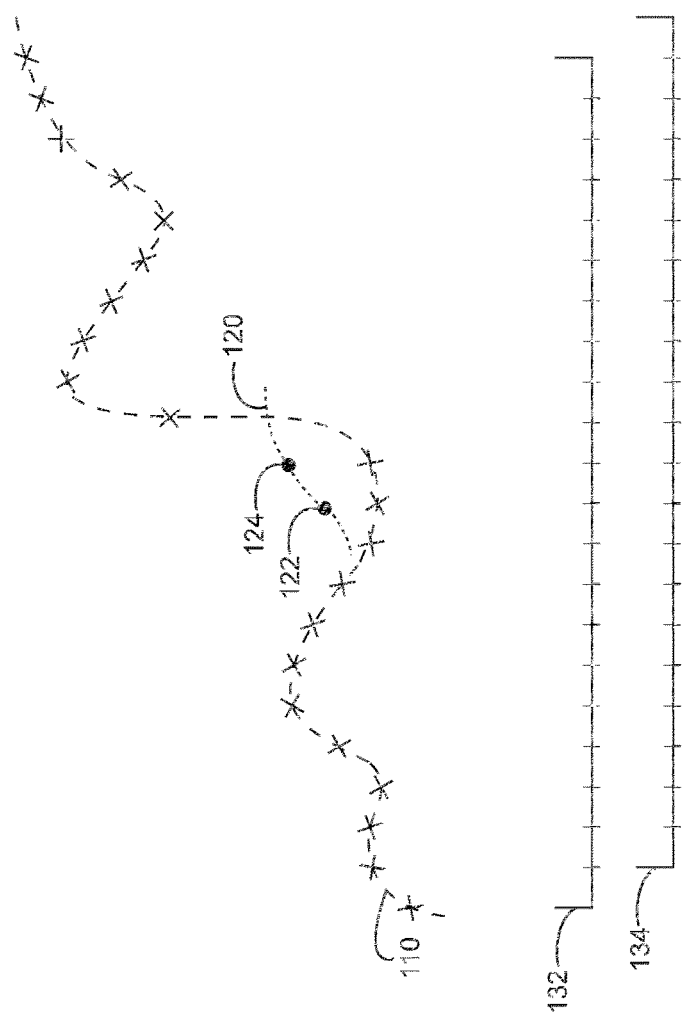
FIG. 2A is an amplitude versus time graph depicting the output of a conventional constant mode averager.
Figure 2B:
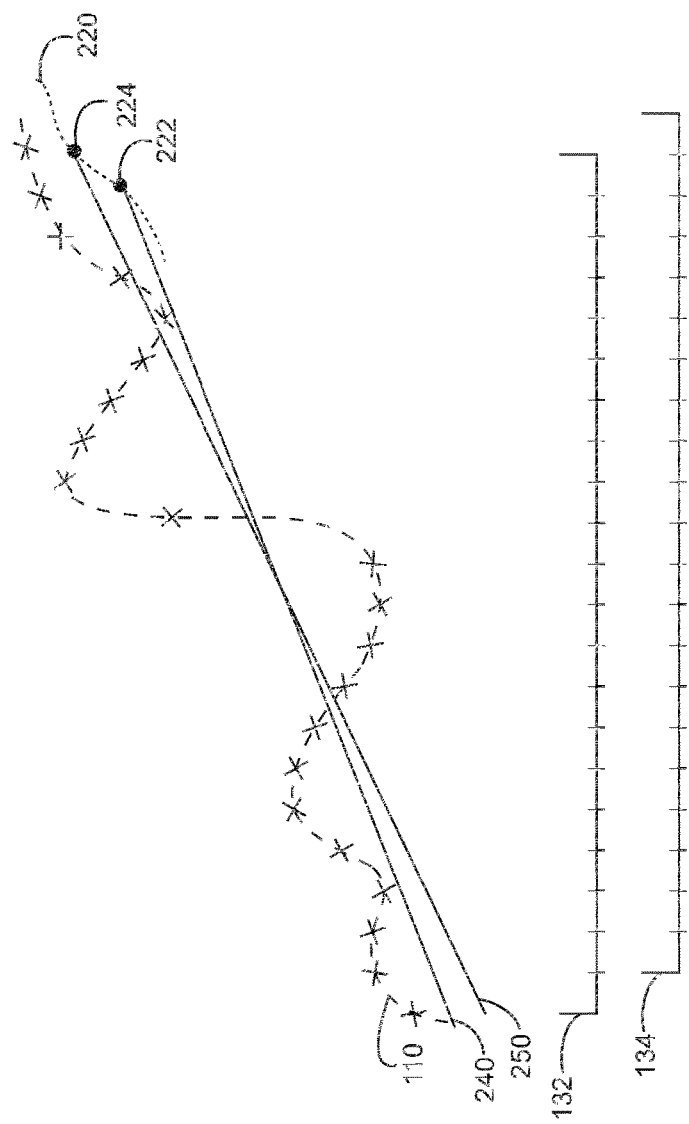
FIG. 2B is an amplitude versus time graph depicting the output of a conventional linear mode averager.
Figure 3:
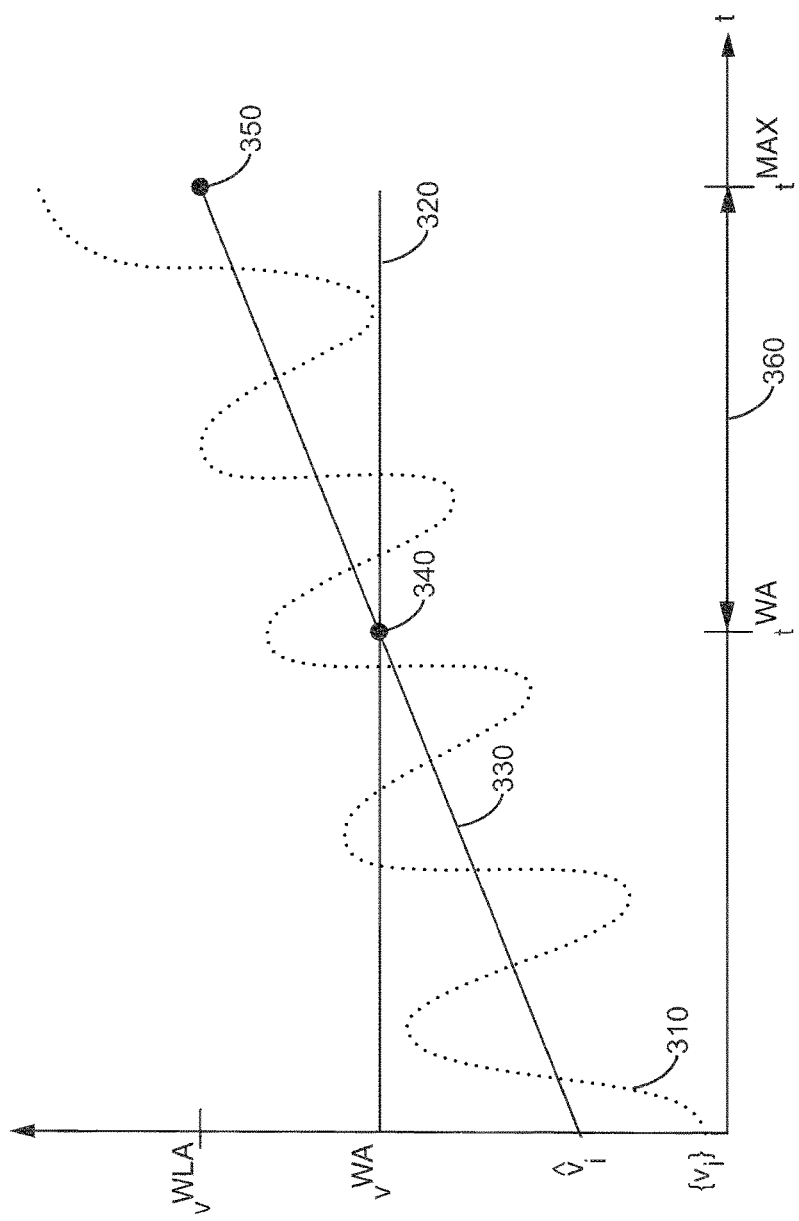
FIG. 3 is an amplitude versus time graph comparing the outputs of a constant mode averager and a linear mode averager.
Figure 4:
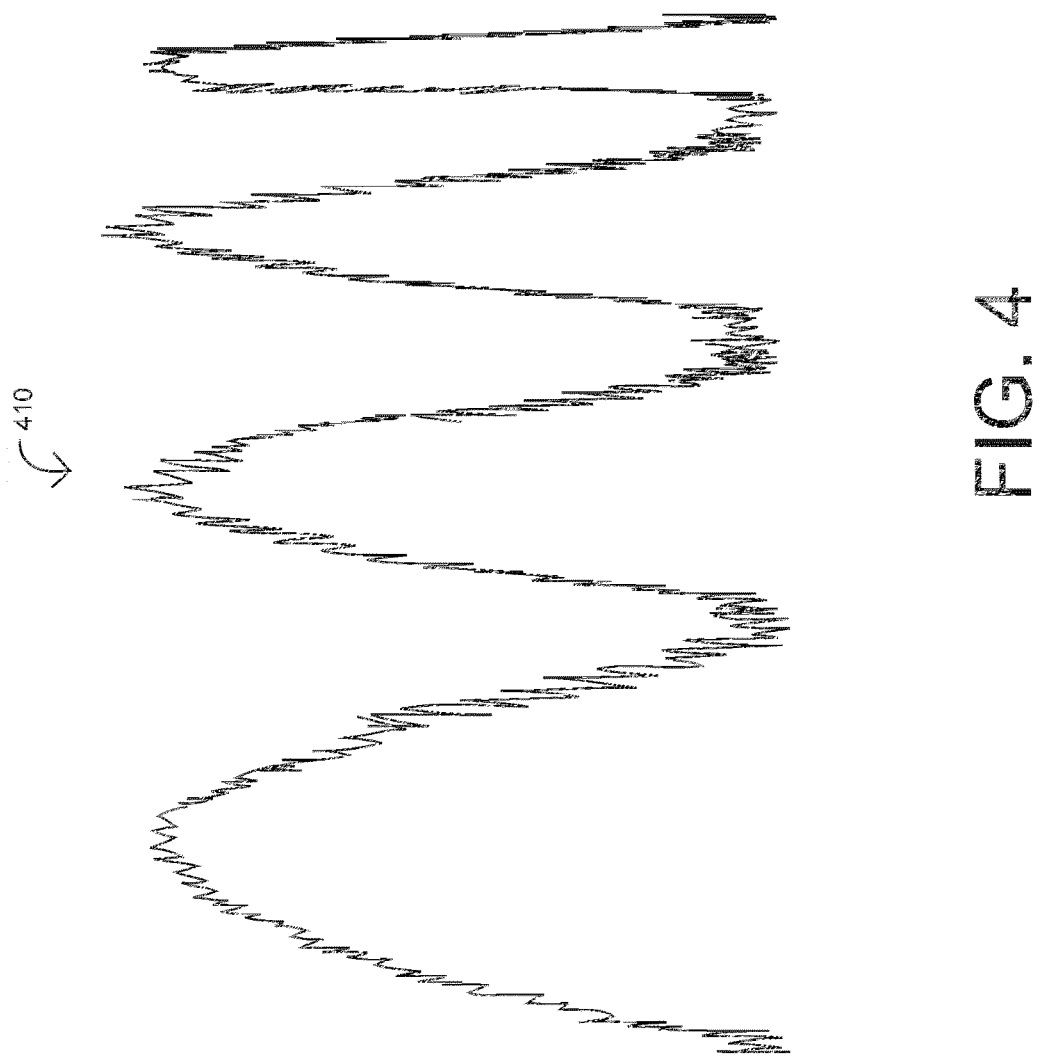
FIG. 4 is an amplitude versus time graph depicting a noisy input signal.
Figure 5:
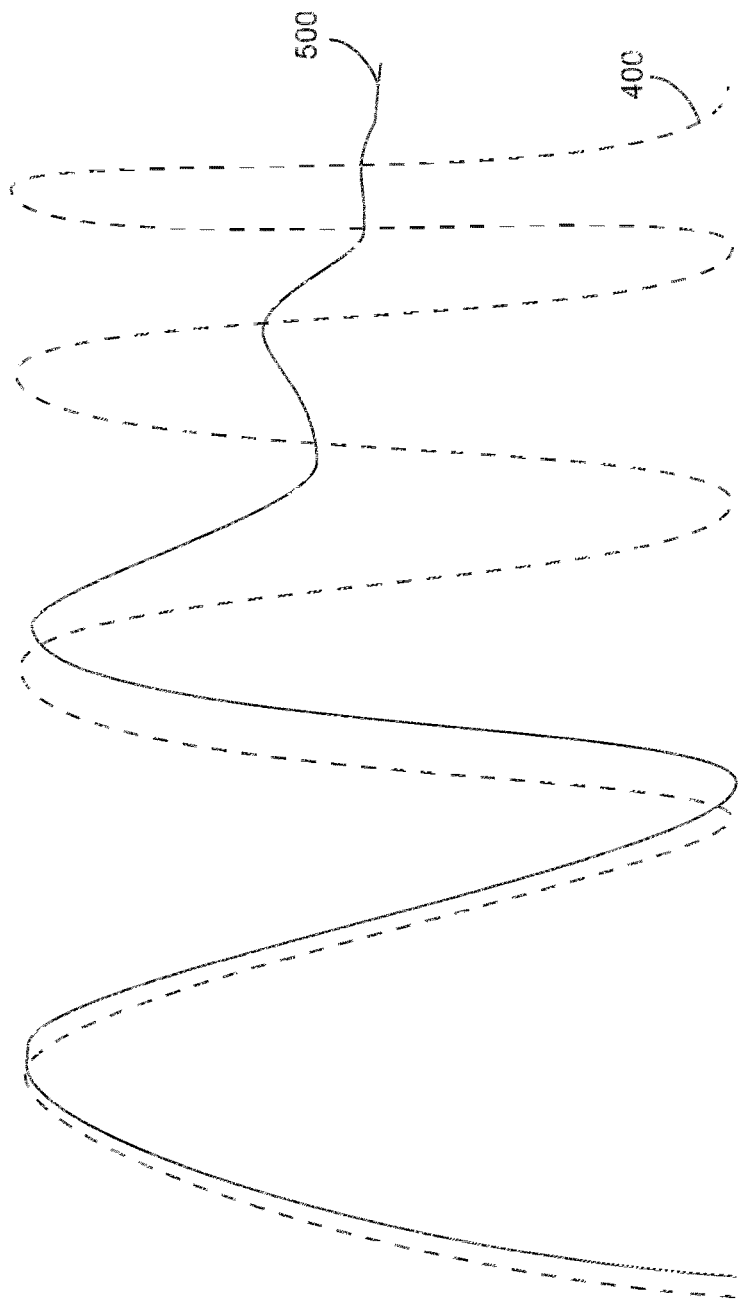
FIG. 5 is an amplitude versus time graph depicting a constant mode averager output signal corresponding to the input signal of FIG. 4.
Figure 6:
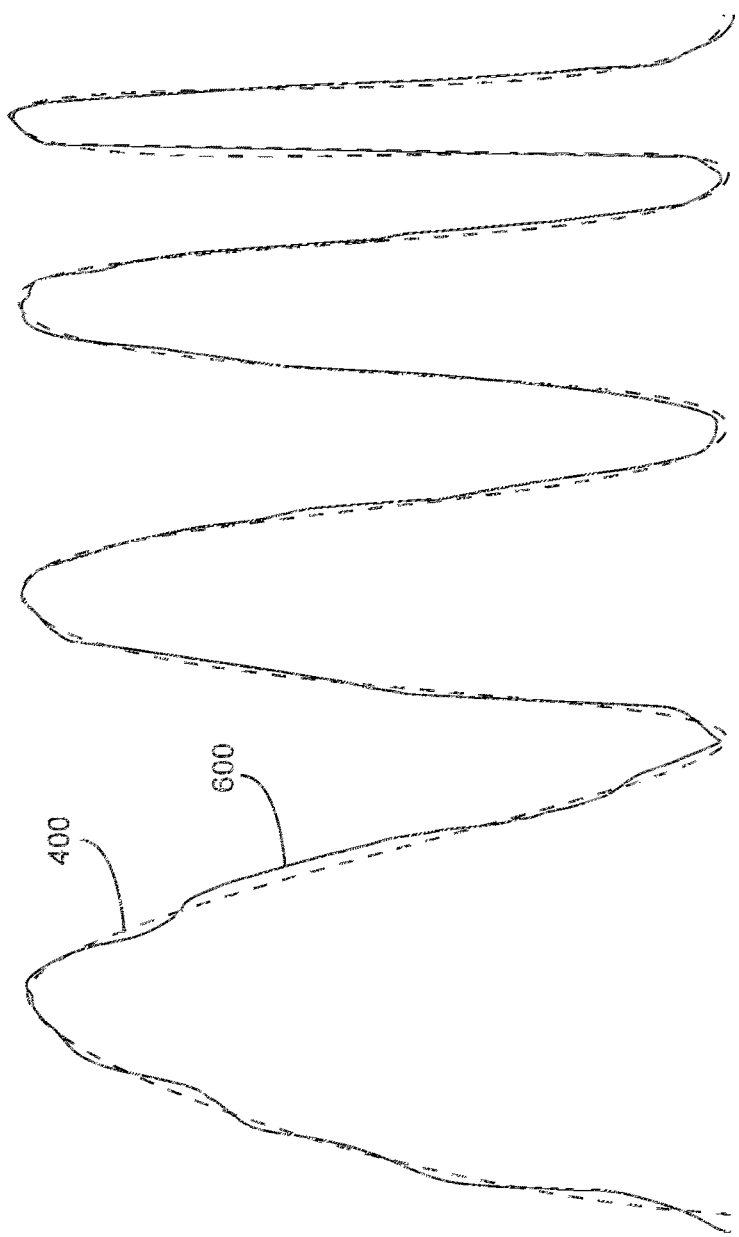
FIG. 6 is an amplitude versus time graph depicting a linear mode averager output signal corresponding to the input signal of FIG. 4.

As shown in FIG. 7, the variable mode averager output 720 is an estimate of the input values at a selected time along the linear fit 710, which indicates a trend of the input values. Assuming 0<mode<1, the mode variable determines the equivalent time 730 between $t^{WA}$ and $t^{MAX}$ for which the estimate is evaluated, yielding an output value 740 between $v^{WA}$ and $v^{WLA}$. Thus, the mode variable acts to parametrically vary the time delay between the input and output signals of the variable mode averager, along with associated output characteristics. If mode=0, the time delay 360 (FIG. 3) is that of the constant mode averager. If mode=1, there is no time delay. If mode>1, the variable mode averager is predicting a future input value based on n past values. In this manner, the variable mode averager can be used to advantageously adjust between the smoothing characteristics of the constant mode averager and the tracking characteristics of the linear mode averager, as described above with respect to FIGS. 4-6. The variable mode control determines how much of each particular characteristic to use for a particular input signal and application. For example, for time periods when the input signal has low confidence, mode can be set further towards zero, although with a time lag penalty. For time periods when the input signal has high confidence or when minimum time lag is required, mode can be set further towards one, or even to a value greater than one.

The variable mode averager has been described in terms of weighted input values. One of ordinary skill, however, will recognize that the present invention includes the case where all of the weights are the same, i.e., where the input values are equally weighted or unweighted. Further, although the variable mode averager has been described in terms of a linear mode averager, one of ordinary skill in the art will recognize that a variable mode averager could also be based on non-linear curve fits, such as exponential or quadratic curves indicating a non-linear trend of the input signal. In addition, one of ordinary skill will understand that the variable mode averager can be implemented to operate on continuous data as well as infinitely long data. Also, a variable mode averager based upon a linear fit by some criteria other than LMS; a variable mode averager using any mode value, including negative values; and a variable mode averager based upon a linear fit where $t^{min}=\min\{t_1, t_2, \ldots, t_n\}$ is substituted for $t^{MAX}$ in equation (22) are all contemplated as within the scope of the present invention.

FIG. 8 illustrates one embodiment 800 of a variable mode signal averager. After an entry point 802, variables are initialized to zero in a block 808. Next, in a block 812, the sums of various parameters are calculated by summing the products of corresponding values in each of three buffers: an input data buffer, value[i]; a weight buffer, weight[i]; and a time value buffer, time[i]. In addition, the weight[i] values are summed. These sums are calculated over the entire length of each buffer, representing a single time window of n values. The calculations are performed by incrementing a loop counter i in a block 810 and reentering the block 812. The loop counter i specifies a particular value in each buffer. Each time through the block 812, the variable mode signal averager generates products of buffer values and adds the results to partial sums. After completing the partial sums, the variable mode signal averager then determines if the ends of the buffers have been reached in a decision block 814 by comparing the incremented value of i to the size of the buffer. If the ends of the buffers have not been reached, the variable mode averager increments the loop counter i and reenters the block 812; otherwise, the variable mode averager continues to a decision block 816.

In the decision block 816, a check is made whether the sum of the weights, sumw, is greater than zero. If so, each of the sums of the products from the block 812 is divided by sumw in a block 820. In the block 820, the parameters computed are:

sumwv, the weighted average value of equation (2);
sumwt, the weighted average time of equation (10);
sumwvt, the weighted average product of value and time; and
sumwt2, the weighted average product of time squared.

The sumwt2 parameter from the block 820 is then used in a block 822 to calculate an autovariance sigma2tt in accordance with equation (18b). If, in a decision block 824, a determination is made that the autovariance is not greater than zero, then in a decision block 825, a determination is made whether the sum of the weights is greater than zero. If, in the decision block 825, the sum of the weights is not greater than zero, then an output value, out, which was initialized to zero in the block 808, is returned as a zero value at a termination point 804. Otherwise, if, in the decision block 825, a determination is made that the sum of the weights is greater than zero, then in a block 826, the value of the sum of the weights is assigned to the output value, out, and the output value is then returned at the termination point 804.

If, in the decision block 824, the autovariance is determined to be greater than zero, then in a block 827, the sumwvt parameter from the block 820 is used to calculate a crossvariance signal sigma2vt in accordance with equation (18a). Thereafter, the maximum time, $t^{MAX}$, as defined in equation (21), is determined by finding the largest time value in the time buffer, time[i]. In particular, in a block 829, the loop counter, i, is reinitialized to zero and the value of $t^{MAX}$ is initialized to zero. Next, in a decision block 832, the current value of $t^{MAX}$ is compared to the current value of the time buffer indexed by the loop counter, i. If the current value of $t^{MAX}$ is not less than the current value of the time buffer or if the current weight value indexed by i is not greater than zero, then $t^{MAX}$ is not changed and a block 834 is bypassed. On the other hand, if the current value of $t^{MAX}$ is less than the current time value and if the current weight value is greater than zero, then the block 834 is entered, and the value of $t^{MAX}$ is replaced with the current time value time[i]. In either case, in a decision block 838, the loop counter, i, is compared to the buffer size, and, if the loop counter, i, is less than the buffer size, the loop counter, i, is incremented in a block 830, and the comparisons are again made in the decision block 832.

When, in the decision block 838, it is determined that the loop counter, i, has reached the buffer size, the variable mode averager proceeds to a block 840 with the largest value of time[i] saved as the value of $t^{MAX}$. In the block 840, a single output value, out, is computed in accordance with equation (22). Thereafter, the output value, out, is limited to the range of values in the input data buffer, value[i]. This is accomplished by comparing out to the maximum and minimum values in the data buffer. First, in a block 850, the maximum of the value buffer is determined. Then, in a decision block 852, the maximum of the value buffer is compared to out. If out is bigger than the maximum of the value buffer, then, in a block 854, out is limited to the maximum value in the buffer. Otherwise, the block 854 is bypassed, and out remains as previously calculated in the block 840. Thereafter, in a block 860, the minimum of the value buffer is determined. The minimum of the value buffer is compared to out in a decision block 862. If out is smaller than the minimum of the value buffer, then, in a block 864, out is set to the minimum value in the buffer. Otherwise, the block 864 is bypassed, and out is not changed. The value of out determined by the block 840, the block 852 or the block 864 is then returned from the routine via the termination point 804.

In one embodiment, the process described with respect to FIG. 8 is implemented as firmware executing on a digital signal processor. One of ordinary skill in the art will recognize that the variable mode averager can also be implemented as a digital circuit. Further, a variable mode averager implemented as an analog circuit with analog inputs and outputs is also contemplated to be within the scope of the present invention.

Pulse oximetry is one application that can effectively use signal processing techniques to provide caregivers with improved physiological measurements. Pulse oximetry is a widely accepted noninvasive procedure for measuring the oxygen saturation level of arterial blood, an indicator of oxygen supply. Early detection of low blood oxygen is critical in the medical field, for example in critical care and surgical applications, because an insufficient supply of oxygen can result in brain damage and death in a matter of minutes. Pulse oximeter systems are described in detail in U.S. Pat. Nos. 5,632,272, 5,769,785, and 6,002,952, which are assigned to the assignee of the present invention and which are incorporated by reference herein.

Figure 9:
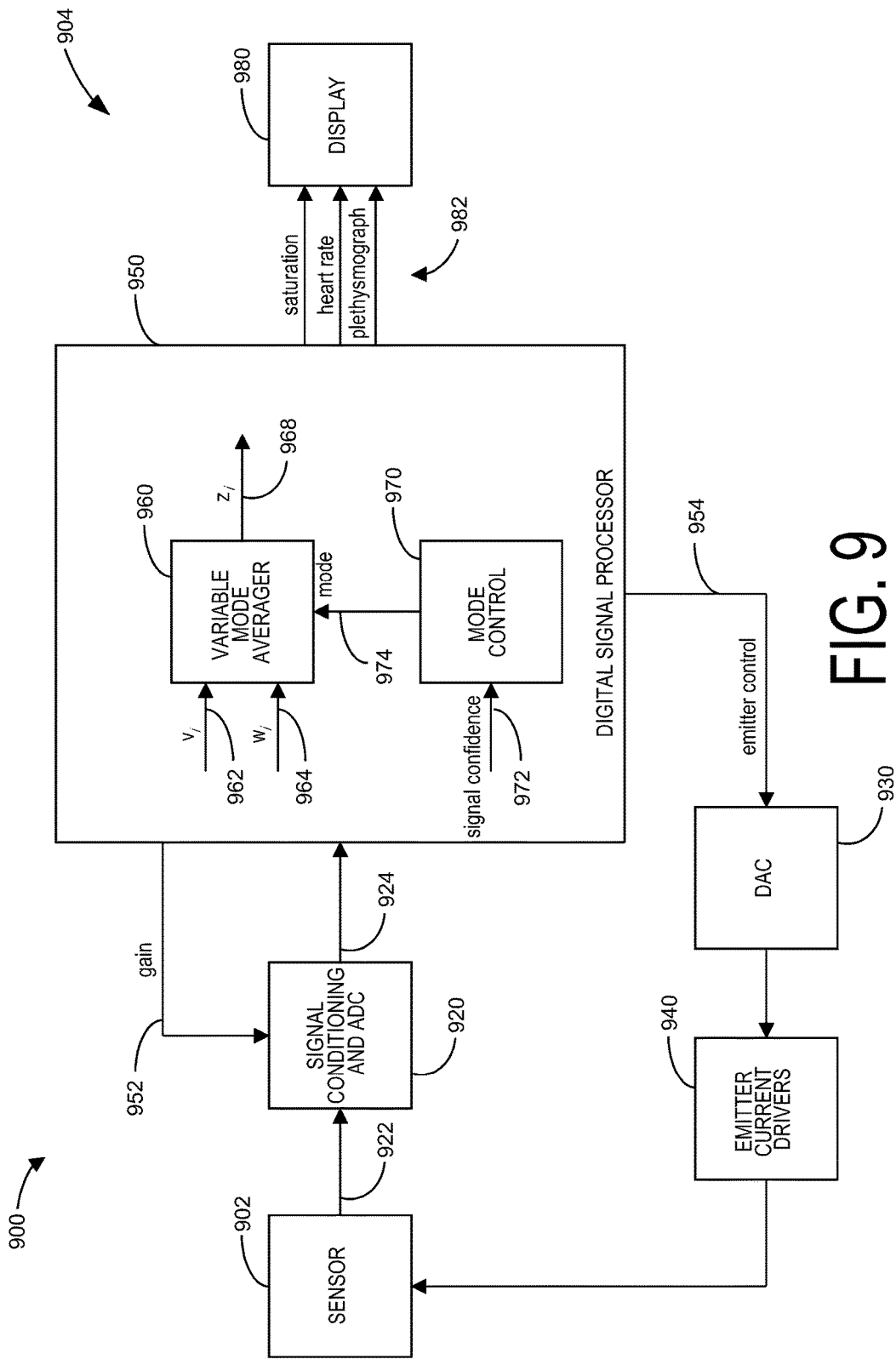
FIG. 9 is a block diagram illustrating a variable mode averager applied to a pulse oximeter.

FIG. 9 depicts a general block diagram of a pulse oximetry system 900 utilizing a variable mode averager 960. A pulse oximetry system 900 consists of a sensor 902 attached to a patient and a monitor 904 that outputs desired parameters 982 to a display 980, including blood oxygen saturation, heart rate and a plethysmographic waveform. Conventionally, a pulse oximetry sensor 902 has both red (RED) and infrared (IR) light-emitting diode (LED) emitters (not shown) and a photodiode detector (not shown). The sensor 902 is typically attached to a patient's finger or toe, or to a very young patient's foot. For a finger, the sensor 902 is configured so that the emitters project light through the fingernail and into the blood vessels and capillaries underneath. The photodiode is positioned at the fingertip opposite the fingernail so as to detect the LED transmitted light as it emerges from the finger tissues, producing a sensor output 922 that indicates arterial blood absorption of the red and infrared LED wavelengths.

As shown in FIG. 9, the sensor output 922 is coupled to analog signal conditioning and an analog-to-digital conversion (ADC) circuit 920. The signal conditioning filters and amplifies the analog sensor output 922, and the ADC provides discrete signal values to the digital signal processor 950. The signal processor 950 provides a gain control 952 to amplifiers in the signal conditioning circuit 920. The signal processor 950 also provides an emitter control 954 to a digital-to-analog conversion (DAC) circuit 930. The DAC 930 provides control signals for the emitter current drivers 940. The emitter drivers 940 couple to the red and infrared LEDs in the sensor 902. In this manner, the signal processor 950 can alternately activate the sensor LED emitters and read the resulting output 922 generated by the photodiode detector.

The digital signal processor 950 determines oxygen saturation by computing the differential absorption by arterial blood of the red and infrared wavelengths emitted by the sensor 902. Specifically, the ADC 920 provides the processor 950 with a digitized input 924 derived from the sensor output 922. Based on this input 924, the processor 950 calculates ratios of detected red and infrared intensities. Oxygen saturation values, $v_i$, are empirically determined based on the calculated red and infrared ratios. These values are an input signal 962 to the variable mode averager 960. Each of the input values, are associated with weights, $w_i$, which form a second input 964 to the averager 960. The individual weights, $w_i$, are indicative of the confidence in particular ones of the corresponding saturation values, $v_i$. A third input 974 sets the mode of the averager 960. The variable mode averager 960 processes the values, $v_i$, weights, $w_i$, and mode as described above with respect to FIGS. 7-8 to generate values, $z_i$. The values $z_i$ are the averager output 968, from which is derived the saturation output 982 to the display 980.

The mode signal may be generated by an external source (not shown) or it may be generated by another function within the digital signal processor. For example, mode may be generated from the confidence level of the input signal as illustrated in FIG. 9. FIG. 9 illustrates a signal confidence input 972 to a mode control process 970. The mode control process 970 maps the signal confidence input 972 to the mode input 974 of the variable mode averager 960. When the signal confidence is low, the mode control 970 sets mode to a relatively small value. Depending on the application, mode may be set close to zero. When the signal confidence is high, the mode control 970 sets mode to a relatively large value. Some applications may prefer a mode of one for a high signal confidence, but this is not a requirement. When the signal confidence is neither high nor low, mode is set to an intermediate value (in some applications, mode may be set to a value between zero and one) empirically to achieve a reasonable tradeoff between a fast saturation output response and saturation accuracy.

The signal quality of pulse oximetry measurements is adversely affected by patients with low perfusion of blood, causing a relatively small detected signal, ambient noise, and artifacts caused by patient motion. The signal confidence input 972 is an indication of the useful range of the pulse oximetry algorithms used by the digital signal processor 950 as a function of signal quality. This useful range is extended by signal extraction techniques that reduce the effects of patient motion, as described in U.S. Pat. Nos. 5,632,272, 5,769,785, and 6,002,952, referenced above. Signal confidence is a function of how well the sensor signal matches pulse oximetry algorithm signal models. For example, the red and infrared signals should be highly correlated and the pulse shapes in the pulsatile red and infrared signals should conform to the shape of physiological pulses, as described in U.S. patent application Ser. No. 09/471,510 filed Dec. 23, 1999, entitled Plethysmograph Pulse Recognition Processor, which is assigned to the assignee of the present invention and which is incorporated by reference herein. As a particular example, signal confidence can be determined by measuring pulse rate and signal strength. If the measured signal strength is within an expected range for the measured pulse rate, then the confidence level will be high. On the other hand, if the measured signal strength is outside the expected range (e.g., too high for the measured pulse rate), then the confidence level will be low. Other measured or calculated parameters can be advantageously used to set the confidence level.

Figure 10:
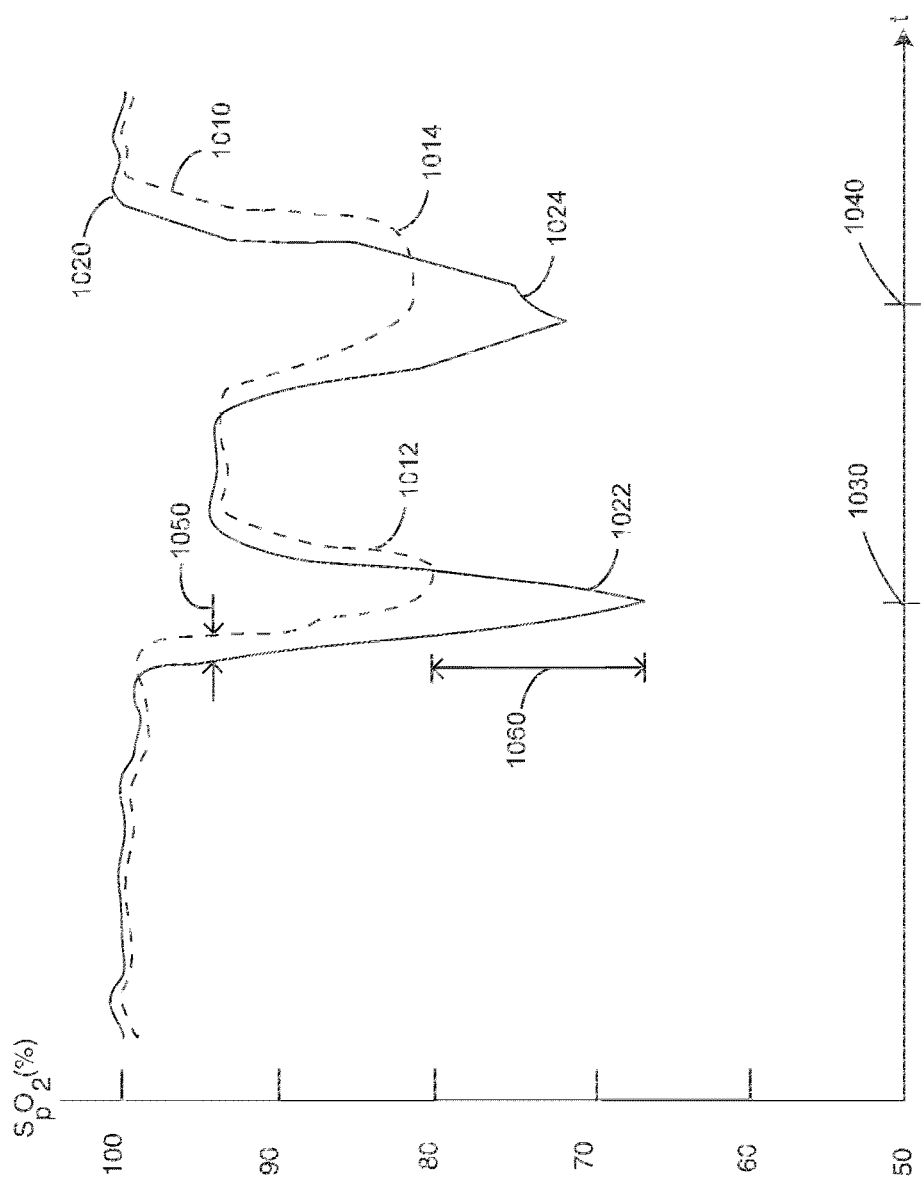
FIG. 10 is an oxygen saturation output versus time graph for a pulse oximeter utilizing a variable mode averager.

FIG. 10 illustrates the oxygen saturation output of a pulse oximeter utilizing a variable mode averager, as described above with respect to FIG. 9. A first output 1010 illustrates oxygen saturation versus time for input oxygen saturation values processed by a conventional weighted averager or, equivalently, by a variable mode averager 960 with mode≈0. A second output 1020 illustrates oxygen saturation versus time for the variable mode averager 960 with mode≈1. Each output 1010, 1020 indicates exemplary desaturation events occurring around a first time 1030 and a second time 1040. The desaturation events correspond to a patient experiencing a potentially critical oxygen supply shortage due to a myriad of possible physiological problems. With mode≈1, the variable mode averager responds to the onset of the desaturation events with less lag time 1050 than that of the conventional weighted average. Further, the variable mode averager responds to the full extent of the desaturations 1060 whereas the conventional weighted average does not. When signal confidence is low, the variable mode averager is adjusted to provide similar smoothing features to those of a conventional weighted average. When signal confidence is high, however, the variable mode averager is advantageously adjusted to respond faster and more accurately to a critical physiological event. The fast response advantage of the variable mode averager has other physiological measurement applications, such as blood-pressure monitoring and ECG.

The variable mode averager has been disclosed in detail in connection with various embodiments of the present invention. One of ordinary skill in the art will appreciate many variations and modifications within the scope of this invention.

Thus, the variable mode averager disclosed in the foregoing advantageously allows a signal processor the ability to reduce a window of input values of, for example, a noisy signal, to a linear fit of estimates of the desired signal, where a selected output value from the estimates corresponds at least in part to the selection of a time or mode. The mode can correspond, for example, to a degree of confidence that the most recently received input signal is an accurate representation of the desired signal. However, a skilled artisan will recognize from the disclosure herein that other mechanisms can be used to reduce a set of input values to one or more appropriate output values.

Figure 11:
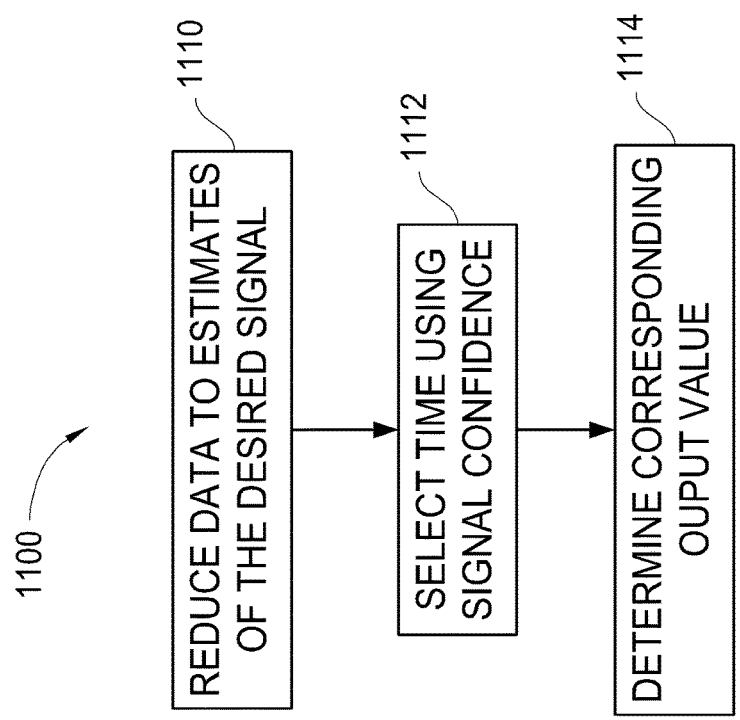
FIG. 11 is a flow chart of an output value selection process of a signal processor, according to an embodiment of the invention.

For example, FIG. 11 illustrates a flow chart of an output value selection process 1100 of a signal processor, according to an embodiment of the invention. As shown in FIG. 11, the process 1100 includes BLOCK 1110, where the signal processor reduces a set or window of input values to one or more or a set of estimates such as the foregoing linear fit of the variable mode averager, or the like. The process 1100 then moves to BLOCK 1112, where the processor selects a time based, for example, on an indication of confidence that the set of input values represents a desired signal. The process 1100 in BLOCK 1114 then determines the output value from the one or more, or set of estimates, which corresponds to the selected time.

As will be appreciated by an artisan from the disclosure herein, a wide variety of processes or mechanisms can be used to reduce a set or window of input data to a set of estimates. For example, the processor can execute the foregoing variable mode averager, or other more conventional signal processing techniques, such as, for example, simple averaging, weighted averaging, linear averaging, filtering, prediction, or the like to reduce the set of input data before selecting an appropriate time using the mode or signal confidence.

Figure 12:
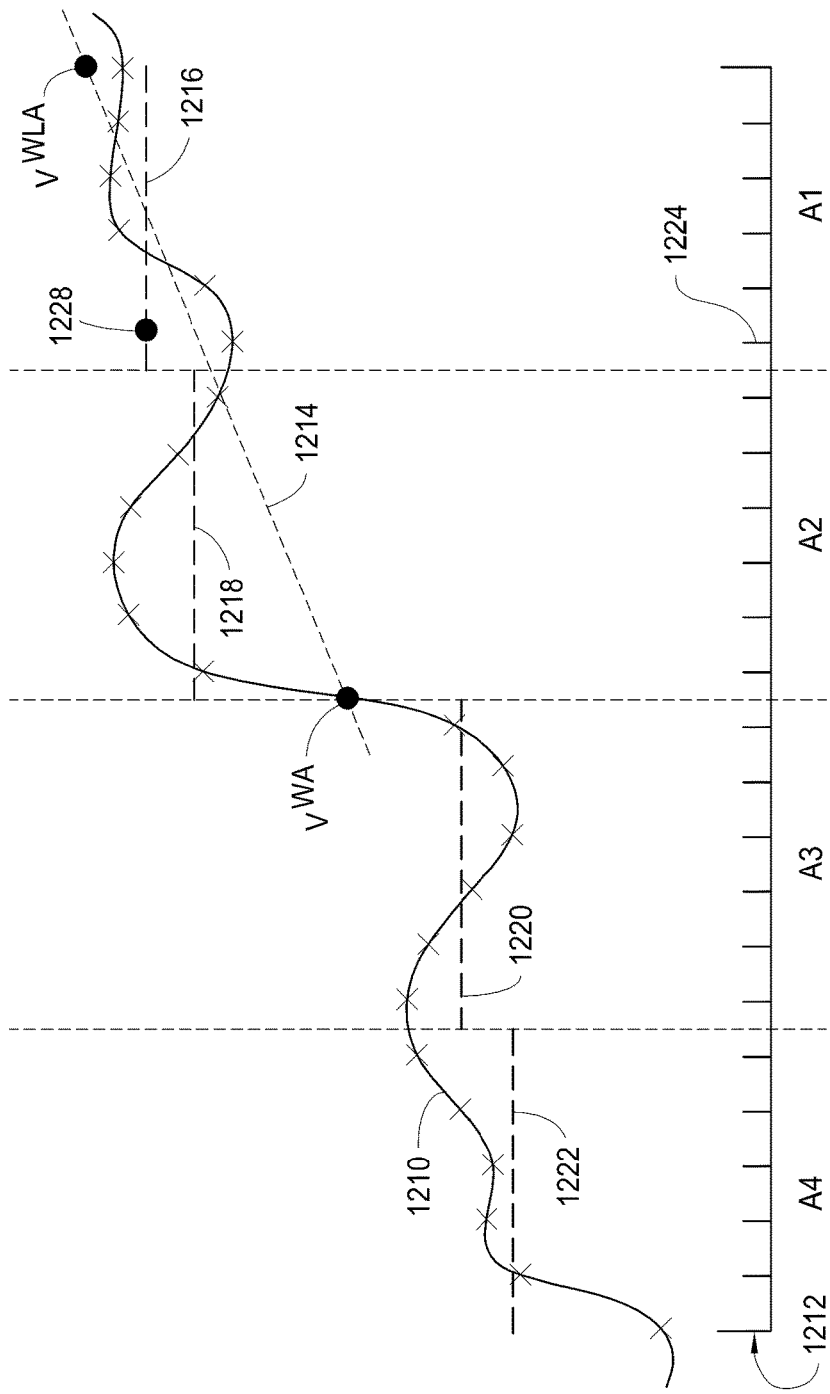
FIG. 12 is an amplitude versus time graph depicting exemplary potential output values of the output value selection process of FIG. 11, according to an embodiment of the invention.

According to one embodiment, the processor can reduce input data through segmentation of a window of input values. For example, FIG. 12 illustrates an amplitude versus time graph depicting an input signal 1210, including a window 1212 of input values. According to one embodiment, the input signal 1210 comprises, for example, a desired signal corrupted by noise or a signal having superfluous features. FIG. 12 shows an example of reduction of the input values corresponding to the window 1212 to the linear fit 1214 of estimates using the foregoing variable mode averager. As disclosed in the foregoing, when 0<mode<1, the mode variable determines the equivalent time along the linear fit of estimates for which an output estimate can be evaluated, thereby yielding an output value between $v^{WA}$ and $v^{WLA}$.

However, FIG. 12 also shows reduction of the input values using segmentation. For example, a signal processor can segment the window 1212 of input values into a plurality of segments, e.g., Segments A1, A2, A3, and A4. A artisan will recognize from the disclosure herein that the use of four segments in FIG. 12 is for illustration only, and the number of segments can be selected based on a number of factors, such as, for example, the number of input values in the window, signal processing speed and capacity, experimental results, or the like.

According to one embodiment, the signal processor then determines one or more or a set of estimates corresponding to each segment. For example, in a straightforward implementation, the signal processor may select simple weighted averages 1216, 1218, 1220, 1222, as estimates for each of the Segments A1, A2, A3, and A4, respectively, of the window 1212 of input values. However, an artisan will recognize from the disclosure herein that the estimates for each segment may range in complexity from simple selection of one or more of the input values, to more complex calculations, such as application of the foregoing variable mode averager or the like for the input values of each segment. Moreover, the artisan will recognize from the disclosure herein that the signal confidence indicator could be used to select one, some, or all of the input values corresponding to one, some, or all, of the segments for the generation of the estimate values.

Once the estimates for each segment are determined, the signal processor selects a time corresponding to a degree of confidence that the input values represent a desired signal. A signal confidence indicator representative of whether the more recently received input signal values are accurate representations of a desired signal can be derived from, for example, an analysis of the amount of noise in the signal, comparing the signal to expected patterns or templates, or the like. The analysis of noise can include a measurement of the entropy of the signal, adherence of the signal to predetermined mathematical models based on a priori information about the expected or desired signal, or the like.

In the example illustrated in FIG. 12, the signal processor may have higher confidence that the estimates from the segmentation are representative of the desired signal, and therefore choose a time 1224 where the estimates 1216-1222 are to be evaluated. According to an embodiment using a more straightforward reduction of the segments, such as, for example, the simple weighted averaging, the signal processor may interpolate between estimates, such as, output value 1228. When more complex mechanisms are used to reduce the input data, determination of the output value 1228 may be directly calculated, such as, for example, calculation of the output value using the variable mode averager. A skilled artisan will also recognize from the disclosure herein that the output value 1228 may comprise an interpolation between more complex estimates, such as, for example, zero, first, second, etc. order interpolation.

Selection of the time 1224 allows the signal processor to slide the output value along, for example, the exemplary line 1214 or one of the segment estimates 1216-1222, thereby providing an output value deemed likely to indicate the value of the desired signal for the most recent input value of the time window 1212. For example, as disclosed in the foregoing, when the signal confidence indicator represents a higher confidence in the input values, the output value 1228 may slide toward the most recent input values, whereas the output value 1228 may side in the opposite direction during a time of lower signal confidence.

The signal processing techniques disclosed in the foregoing, which use a confidence measure to select an output value from a set of estimates of a window of input values, is particular applicable to the monitoring of critical physiological parameters in patient-care settings. When applied to pulse oximeter oxygen saturation measurements, the mode parameter can be varied in real-time to achieve a tradeoff between the suppression of false alarms and signal artifacts and the immediate detection of life threatening oxygen desaturation events. For example, during the monitoring of physiological parameters, it is often common for motion artifacts or other abnormalities to appear in the input value stream. Such abnormalities often decrease the confidence measure, or mode, being used by the signal processor. As disclosed in the foregoing, a lower signal confidence may lead to the signal processor selecting a smoothed output estimate for a specific time window, such as for example, time windows ranging from approximately 15 seconds to over 1 minute, thereby avoiding crossing over alarm-activating output thresholds. Alternatively, as discussed with reference to FIG. 10, a signal abnormality accompanied by high signal confidence leads the signal processor to the selection of an output estimate that more accurately reflects the extent of a potentially life threatening desaturation event, thereby ensuring an appropriate alarm activation.

Although the foregoing invention has been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. Accordingly, the present invention is not intended to be limited by the reaction of the preferred embodiments which disclose by way of example only, but is to be defined by reference to the appended claims.

Additionally, all publications, patents, and patent applications mentioned in this specification are herein incorporated by reference to the same extent as if each individual publication, patent, or patent application was specifically and individually indicated to be incorporated by reference.

What is claimed is:

1. A pulse oximetry system, the pulse oximetry system comprising:
   an analog signal conditioning circuit that receives signals corresponding to attenuated red and infrared light transmitted through body tissue of a patient, the analog signal conditioning circuit comprising an analog-to-digital conversion circuit that provides first discrete signal values at a first time and second discrete signal values at a second time;
   a digital-to-analog conversion circuit that provides control signals to emitter current drivers to cause the red and infrared light to transmit through the body tissue; and
   a digital signal processor that:
      receives the first discrete signal values and the second discrete signal values from the analog signal conditioning circuit, the first discrete signal values having a first amount of noise greater than a second amount of noise of the second discrete signal values;
      outputs an emitter control signal to the digital-to-analog conversion circuit;
      calculates first oxygen saturation values based on the first discrete signal values and second oxygen saturation values based on the second discrete signal values, the first and second oxygen saturation values corresponding with oxygen saturation of the patient's blood;
      adjusts the first oxygen saturation values to produce first adjusted oxygen saturation values by smoothing the first oxygen saturation values, wherein the digital signal processor determines to use said smoothing based at least in part on the first amount of noise;
      adjusts the second oxygen saturation values to produce second adjusted oxygen saturation values by applying a curve-fit to the second oxygen saturation values, wherein the digital signal processor determines to use the curve-fit based at least in part on the second amount of noise; and
      outputs the first and second adjusted oxygen saturation values to a display.

2. The system of claim 1, wherein the digital signal processor computes a first signal confidence based on the first amount of noise and a second signal confidence based on the second amount of noise.

3. The system of claim 2, wherein the digital signal processor determines to use said smoothing based on the first signal confidence, and wherein the digital signal processor determines to use the curve-fit based on the second signal confidence.

4. The system of claim 2, wherein the digital signal processor computes the first signal confidence based at least in part by measuring pulse rate and signal strength of the first discrete signal values.

5. The system of claim 4, wherein the digital signal processor computes a higher value of the first signal confidence when the signal strength is within an expected range for the measured pulse rate or a lower value of the first signal confidence when the signal strength is outside an expected range for the measured pulse rate.

6. The system of claim 4, wherein the digital signal processor performs said smoothing by determining a moving weighted average of the first oxygen saturation values.

7. The system of claim 4, wherein the curve-fit is a non-linear curve fit.

8. The system of claim 7, wherein the non-linear curve fit is an exponential curve fit.

9. A system comprising:
   an analog signal conditioning circuit that receives signals corresponding to attenuated light transmitted through body tissue of a patient, the analog signal conditioning circuit comprising an analog-to-digital conversion circuit that provides first discrete signal values at a first time and second discrete signal values at a second time subsequent to the first time;
   a digital-to-analog conversion circuit that provides control signals to emitter current drivers to cause the light to transmit through the body tissue; and
   a processor that:
      receives the first discrete signal values and the second discrete signal values from the analog signal conditioning circuit;
      calculates first physiological parameter values based on the first discrete signal values and second physiological parameter values based on the second discrete signal values;
      calculate a first signal confidence based on first noise in the first discrete signal values and a second signal confidence based on second noise in the second discrete signal values;
      adjusts the first physiological parameter values to produce first adjusted physiological parameter values by smoothing the first physiological parameter values, wherein the processor uses said smoothing based at least in part on the first signal confidence;
      adjusts the second physiological parameter values to produce second adjusted physiological parameter values by applying filtering to the second physiological parameter values, wherein the processor uses said filtering based at least in part on the second signal confidence;
      wherein the processor uses said smoothing instead of said filtering for the first physiological parameter values based on the first signal confidence being lower than the second signal confidence; and
      provide the first and second adjusted physiological parameter values for output to a display.

10. The system of claim 9, wherein the filtering comprises non-linear filtering.

11. The system of claim 10, wherein the filtering comprises exponential filtering.

12. The system of claim 9, wherein the smoothing comprises averaging.

13. The system of claim 9, wherein the filtering comprises curve-fitting.

14. The system of claim 9, wherein the processor uses said filtering instead of said smoothing for the second physiological parameter values based on the second signal confidence being higher than the first signal confidence.

15. The system of claim 9, wherein the processor calculates third physiological parameter values and adjusts the third physiological parameter values with a combination of smoothing and filtering.

16. The system of claim 15, wherein the combination of smoothing and filtering comprises applying a single equation that incorporates both averaging and curve fitting.

\* \* \* \* \*